United States Patent
Kim et al.

(10) Patent No.: US 12,011,420 B2
(45) Date of Patent: Jun. 18, 2024

(54) COMPOSITIONS AND METHODS FOR TREATMENT OF MICROBIAL INFECTIONS

(71) Applicant: EpiTop, Inc., Poway, CA (US)

(72) Inventors: Byung Eui Kim, Greenwood Village, CO (US); Donald Y. M. Leung, Denver, CO (US)

(73) Assignee: EpiTop, Inc., Poway, CA (US)

( * ) Notice: Subject to any disclaimer, the term of this patent is extended or adjusted under 35 U.S.C. 154(b) by 0 days.

(21) Appl. No.: 18/046,127

(22) Filed: Oct. 12, 2022

(65) Prior Publication Data

US 2024/0122872 A1    Apr. 18, 2024

(51) Int. Cl.
    *A61K 31/015*    (2006.01)
    *A61P 31/04*    (2006.01)

(52) U.S. Cl.
    CPC ............ *A61K 31/015* (2013.01); *A61P 31/04* (2018.01)

(58) Field of Classification Search
    CPC ......... A61K 31/015; A61P 31/27; A61P 31/14
    See application file for complete search history.

(56) References Cited

U.S. PATENT DOCUMENTS

| | | | |
|---|---|---|---|
| 10,226,435 B2 | 3/2019 | Burns et al. | |
| 2015/0017227 A1 | 1/2015 | Kim et al. | |
| 2019/0224193 A1 | 7/2019 | Reid et al. | |
| 2022/0370535 A1* | 11/2022 | Erdogmus | A61K 36/61 |

FOREIGN PATENT DOCUMENTS

WO    WO-2004112819 A1    12/2004

OTHER PUBLICATIONS

Loizzo et al. Phytochemical Analysis and in vitro Antiviral Activities of the Essential Oils of Seven Lebanon Species. Chemistry & Biodiversity, vol. 5, 461-470. (Year: 2008).*
Bielach-Bazyluk et al.: Sirtuin 1 and Skin: Implications in Intrinsic and Extrinsic Aging—A Systematic Review. Cells. 2021 10(4):813, pp. 1-21 doi:10.3390/cells10040813 (2021).
Blander et al.: SIRT1 promotes differentiation of normal human keratinocytes. J Invest Dermatol. 129(1):41-49 doi:10.1038/jid.2008.179 (2009).
Busse et al.: A synthetic sandalwood odorant induces wound-healing processes in human keratinocytes via the olfactory receptor OR2AT4. J Invest Dermatol. 134(11):2823-2832 doi:10.1038/jid.2014.273 (2014).
Carretero et al.: In vitro and in vivo wound healing-promoting activities of human cathelicidin LL-37. J Invest Dermatol. 128(1):223-236 doi:10.1038/sj.jid.5701043 (2008).
Co-pending U.S. Appl. No. 18/046,125, inventors Kim; Byung Eui et al., filed Oct. 12, 2022.
Gibson et al.: Nonviral human beta defensin-3 expression in a bioengineered human skin tissue: a therapeutic alternative for infected wounds. Wound Repair Regen. 20(3):414-424 doi:10.1111/j.1524-475X.2012.00786.x (2012).
Hildenbrand et al.: Impaired skin regeneration and remodeling after cutaneous injury and chemically induced hyperplasia in taps-transgenic mice. J Invest Dermatol. 130(7):1922-1930 doi:10.1038/jid.2010.54 (2010).
Hirsch et al.: Human beta-defensin-3 promotes wound healing in infected diabetic wounds. J Gene Med. 11(3):220-228 doi:10.1002/jgm.1287 (2009).
Nakatsuji et al.: Antimicrobial peptides: old molecules with new ideas. J Invest Dermatol. 132(3 Pt 2):887-895 doi:10.1038/jid.2011.387 (2012).
Qiang et al.: Epidermal SIRT1 regulates inflammation, cell migration, and wound healing. Sci Rep. 7(1):14110:1-10 doi:10.1038/s41598-017-14371-3 (2017).
Resing et al.: Multiple copies of phosphorylated filaggrin in epidermal profilaggrin demonstrated by analysis of tryptic peptides. Biochemistry. 24(15):4167-4175 doi:10.1021/bi00336a053 (1985).
Wang et al.: Impaired DNA damage response, genome instability, and tumorigenesis in SIRT1 mutant mice. Cancer Cell. 14(4):312-323 doi:10.1016/j.ccr.2008.09.001 (2008).
Kim et al.: Particulate matter causes skin barrier dysfunction. JCI Insight 6(5):e145185:1-17 doi:10.1172/jci.insight.145185 (2021).
Kim et al.: Skin Wound Healing Is Accelerated by a Lipid Mixture Representing Major Lipid Components of Chamaecyparis obtusa Plant Extract. J Invest Dermatol. 138(5): 1176-1186 doi:10.1016/j.jid.2017.11.039 (2018).

* cited by examiner

*Primary Examiner* — Sikarl A Witherspoon
(74) *Attorney, Agent, or Firm* — WILSON SONSINI GOODRICH & ROSATI

(57) ABSTRACT

Provided are a pharmaceutical composition and a method for treating a microbial infection in a subject in need thereof. In some cases, the composition comprises at least about 10% of thujopsene and at least about 10% of totarol. The present disclosure also provides a pharmaceutical composition and a method for treating a viral infection in a subject in need thereof. In some cases, the method comprises administering to the subject in need thereof a therapeutically effective amount of a composition comprising at least about 10% of thujopsene.

14 Claims, 9 Drawing Sheets

COMPOSITIONS AND METHODS FOR TREATMENT OF MICROBIAL INFECTIONS

BACKGROUND

The microorganisms (microbes) including bacteria, viruses, fungi, and parasites can cause a wide range of diseases in different forms. These days people are infected with various microbes worldwide. Unfortunately, many of these individuals are unable to clear their infection with the current standard of care. Moreover, conventional treatments are associated with different side effects, precluding its use by many individuals. For most viral infections, treatments can only help with symptoms while the patient waits for the immune system to fight off the virus. Antibiotics do not work for viral infections. The antiviral medicines can ease symptoms and shorten the length of a viral infection. Despite continuous efforts to develop the treatments of microbial infections, there remains an unmet need for approaches that overcome inherent limitations of conventional methods to effectively treat them.

SUMMARY

In one aspect, this disclosure provides a method for treating a viral infection in a subject in need thereof. In some embodiments, the method comprises administering to the subject a therapeutically effective amount of a composition comprising at least about 10% of thujopsene. In some embodiments, the composition comprises at least about 30% of thujopsene. In some embodiments, the composition comprises at least about 50% of thujopsene. In some embodiments, the composition comprises at least about 70% of thujopsene. In some embodiments, the composition comprises at least about 90% of thujopsene. In some embodiments, the thujopsene has a purity of at least about 80%. In some embodiments, the thujopsene has a purity of at least about 90%. In some embodiments, the thujopsene has a purity of at least about 95%. In some embodiments, the purity of thujopsene is determined by HPLC.

In some embodiments, the viral infection is caused by a herpesvirus (HSV). In some embodiments, the HSV comprises HSV-1, HSV-2, varicella-zoster virus (VZV), Epstein-Barr virus (EBV), human cytomegalovirus (HCMV), human herpesvirus 6A (HHV-6A), human herpesvirus 6B (HHV-6B), human herpesvirus 7 (HHV-7), or Kaposi's sarcoma-associated herpesvirus (KSHV). In some embodiments, the viral infection is caused by a poxvirus. In some embodiments, the poxvirus comprises smallpox virus (variola), vaccinia virus, cowpox virus, monkeypox virus, orf virus, pseudocowpox virus, bovine popular stomatitis virus, tanapox virus, yaba monkey tumor virus, or molluscum contagiosum virus. In some embodiments, the viral infection is caused by a coronavirus. In some embodiments, the coronavirus comprises 229E, NL63, OC43, or HKU1. In some embodiments, the coronavirus comprises MERS-CoV, SARS-CoV, SARS-CoV-2, or a variant thereof.

In some embodiments, administering the composition decreases or reduces viral titer in the subject. In some embodiments, the viral titer in the subject is measured by determining the number of plaque forming units (pfu) in a cell in the subject. In some embodiments, the viral titer in the subject is decreased or reduced by at least about 10%, 20%, 30%, 40%, 50%, 60%, 70%, 80%, or 90% within 2 hours after the administration. In some embodiments, the viral titer in the subject is decreased or reduced by at least about 10%, 20%, 30%, 40%, 50%, 60%, 70%, 80%, or 90% within 4 hours after the administration. In some embodiments, the composition decreases or reduces the activity of viruses in the subject. In some embodiments, the activity of viruses in the subject is decreased or reduced by at least about 10%, 20%, 30%, 40%, 50%, 60%, 70%, 80%, or 90% within 2 hours after the administration. In some embodiments, the activity of viruses in the subject is decreased or reduced by at least about 10%, 20%, 30%, 40%, 50%, 60%, 70%, 80%, or 90% within 4 hours after the administration. In some embodiments, the composition decreases or reduces viral gene expression in the subject. In some embodiments, the gene expression of viruses in the subject is decreased or reduced by at least about 10%, 20%, 30%, 40%, 50%, 60%, 70%, 80%, or 90% within 2 hours after the administration. In some embodiments, the gene expression of viruses in the subject is decreased or reduced by at least about 10%, 20%, 30%, 40%, 50%, 60%, 70%, 80%, or 90% within 4 hours after the administration.

In some embodiments, the composition prevents, inhibits, or slows the destruction of a cell in the subject. In some embodiments, the cell comprises fibroblast. In some embodiments, the therapeutically effective amount of the composition is administered one to five times a day. In some embodiments, the therapeutically effective amount of the composition is administered two times a day. In some embodiments, the therapeutically effective amount of the composition is administered three times a day. In some embodiments, the therapeutically effective amount of the composition is administered for at least five consecutive days. In some embodiments, the therapeutically effective amount of the composition is administered for at least seven consecutive days. In some embodiments, the therapeutically effective amount of the composition is administered at least for about 15 days, about 21 days, about 24 days, about 28 days, or about 30 days. In some embodiments, the therapeutically effective amount of the composition comprises from about 0.001% to about 0.04% of concentration. In some embodiments, the therapeutically effective amount of the composition comprises from about 0.005% to about 0.02% of concentration. In some embodiments, the therapeutically effective amount of the composition comprises from about 0.005% to about 0.04% of concentration. In some embodiments, the therapeutically effective amount of the composition comprises from about 0.01% to about 0.02% of concentration.

In some embodiments, the administering comprises topical administration or transdermal administration. In some embodiments, the topical administration comprises administration of the composition to an affected skin area. In some embodiments, the topical administration comprises administering an ointment, cream, suspensions, paste, lotions, powders, solutions, oils, encapsulated gel, liposomes, sprayable aerosol or vapors, or any combination thereof.

In another aspect, the disclosure provides a pharmaceutical composition for treating a microbial infection in a subject in need thereof. In some embodiments, the composition comprising thujopsene and totarol, wherein the composition comprises at least about 10% of thujopsene and at least about 10% of totarol. In some embodiments, the total volume amount of thujopsene and totarol in the composition comprises at least about 20%, 40%, 60%, 80%, or 90%. In some embodiments, the volume amount of thujopsene is higher than the volume amount of totarol. In some embodiments, the thujopsene has a purity of at least about 80%. In some embodiments, the thujopsene has a purity of at least about 90%. In some embodiments, the thujopsene has a purity of at least about 95%. In some embodiments, the totarol has a purity of at least about 80%. In some embodiments, the totarol has a purity of at least about 90%. In some embodiments, the totarol has a purity of at least about 95%. In some embodiments, the purity of thujopsene is determined by HPLC.

In some embodiments, the composition further comprises at least one pharmaceutically acceptable carrier, at least one diluent, at least one excipient or at least one additive. In some embodiments, the at least one pharmaceutically acceptable carrier is selected from the group consisting of: dimethyl sulfoxide (DMSO), alpha-thujene, alpha-pinene, camphene, sabinene, beta-pinene, alpha-terpinene, benzene, limonene, peltay2-carene, trans sabinene hydrate, terpinolene, 3-cyclohexen-1-ol, terpinene-4-ol, 1,2-benzenediol, linalyl acetae, borneol, bornyl acetate, alph-thujone, terpinyl acetate, isolongifolene, epit-bicyclosesquiphellandrene, alpha-humulene, guaiol, elemol, cedrol, beta-eudesmol, rosifoliol, rimuene, hexadecanoic acid, cembrene, verticellol, totarol, totara-1,9-octadecenamide, tatarol, 2-(hexylthiol)decanal, and combinations thereof.

In some embodiments, the at least one diluent comprises buffer, saline, water, DMSO, lactose, or combinations thereof. In some embodiments, the at least one excipient is selected from the group consisting of: animal and vegetable fats, oils, waxes, paraffins, starch, tragacanth, cellulose derivatives, polyethylene glycols, silicones, bentonites, silicic acid, talc, zinc oxide, lactose, talc, silicic acid, aluminum hydroxide, calcium silicates, polyamide powder, and combinations thereof. In some embodiments, the at least one additive is selected from the group consisting of: a fatty substance, an organic solvent, a solubilizing agent, a thickener, a gelling agent, a softener, an antioxidant, a suspending agent, a stabilizer, a foaming agent, an aromatic, a surfactant, water, an ionic or non-ionic emulsifying agent, a filler, a sequestering agent, a chelating agent, a preservative, vitamins, a blocker, a moisturizing agent, essential oil, a dye, a pigment, a hydrophilic or hydrophobic activator, a lipid vesicle, antiseptics, stabilizing agents, hydrating agents, emulsification promoters or salts and/or buffers for osmotic control, and combinations thereof.

In some embodiments, the microbial infection comprises a bacterial infection. In some embodiments, the bacterial infection is caused by *Staphylococcus aureus*. In some embodiments, the bacterial infection is caused by methicillin-resistant staph (MRSA), methicillin-susceptible staph (MSSA), or a combination thereof. In some embodiments, the bacterial infection is caused by *Streptococcus*. In some embodiments, the bacterial infection is caused by *Streptococcus pyogenes, Streptococcus dysgalactiae, Streptococcus anginosus*, or a combination thereof.

Provided herein in one embodiment is also a method for treating a microbial infection in a subject in need thereof. In some embodiments, the method comprises administering to the subject a therapeutically effective amount of a composition comprising thujopsene and totarol, wherein the composition comprises at least about 10% of thujopsene and at least about 10% of totarol. In some embodiments, the total volume amount of thujopsene and totarol in the composition comprises at least about 20%, 40%, 60%, 80%, or 90%. In some embodiments, the volume amount of thujopsene is higher than the volume amount of totarol. In some embodiments, the thujopsene has a purity of at least about 80%. In some embodiments, the thujopsene has a purity of at least about 90%. In some embodiments, the thujopsene has a purity of at least about 95%. In some embodiments, the totarol has a purity of at least about 80%. In some embodiments, the totarol has a purity of at least about 90%. In some embodiments, the totarol has a purity of at least about 95%. In some embodiments, the purity of thujopsene is determined by HPLC.

In some embodiments, the composition further comprises at least one pharmaceutically acceptable carrier, at least one diluent, at least one excipient or at least one additive. In some embodiments, the at least one pharmaceutically acceptable carrier is selected from the group consisting of: dimethyl sulfoxide (DMSO), alpha-thujene, alpha-pinene, camphene, sabinene, beta-pinene, alpha-terpinene, benzene, limonene, peltay2-carene, trans sabinene hydrate, terpinolene, 3-cyclohexen-1-ol, terpinene-4-ol, 1,2-benzenediol, linalyl acetae, borneol, bornyl acetate, alph-thujone, terpinyl acetate, isolongifolene, epit-bicyclosesquiphellandrene, alpha-humulene, guaiol, elemol, cedrol, beta-eudesmol, rosifoliol, rimuene, hexadecanoic acid, cembrene, verticellol, totarol, totara-1,9-octadecenamide, tatarol, 2-(hexylthiol)decanal, and combinations thereof. In some embodiments, the at least one diluent comprises buffer, saline, water, DMSO, lactose, or combinations thereof. In some embodiments, the at least one excipient is selected from the group consisting of: animal and vegetable fats, oils, waxes, paraffins, starch, tragacanth, cellulose derivatives, polyethylene glycols, silicones, bentonites, silicic acid, talc, zinc oxide, lactose, talc, silicic acid, aluminum hydroxide, calcium silicates, polyamide powder, and combinations thereof. In some embodiments, the at least one additive is selected from the group consisting of: a fatty substance, an organic solvent, a solubilizing agent, a thickener, a gelling agent, a softener, an antioxidant, a suspending agent, a stabilizer, a foaming agent, an aromatic, a surfactant, water, an ionic or non-ionic emulsifying agent, a filler, a sequestering agent, a chelating agent, a preservative, vitamins, a blocker, a moisturizing agent, essential oil, a dye, a pigment, a hydrophilic or hydrophobic activator, a lipid vesicle, antiseptics, stabilizing agents, hydrating agents, emulsification promoters or salts and/or buffers for osmotic control, and combinations thereof.

In some embodiments, the microbial infection comprises a bacterial infection. In some embodiments, the bacterial infection is caused by *Staphylococcus aureus*. In some embodiments, the bacterial infection is caused by methicillin-resistant staph (MRSA), methicillin-susceptible staph (MSSA), or a combination thereof. In some embodiments, the bacterial infection is caused by *Streptococcus*. In some embodiments, the bacterial infection is caused by *Streptococcus pyogenes, Streptococcus dysgalactiae, Streptococcus anginosus*, or a combination thereof.

In some embodiments, the composition decreases or reduces the activity of bacteria in the subject. In some embodiments, the activity of bacteria in the subject is decreased or reduced by at least about 10%, 20%, 30%, 40%, 50%, 60%, 70%, 80%, or 90% within 2 hours after the administration. In some embodiments, the activity of bacteria in the subject is decreased or reduced by at least about 10%, 20%, 30%, 40%, 50%, 60%, 70%, 80%, or 90% within 4 hours after the administration. In some embodiments, the therapeutically effective amount of the composition is administered one to five times a day. In some embodiments, the therapeutically effective amount of the composition is administered two times a day. In some embodiments, the therapeutically effective amount of the composition is administered three times a day. In some embodiments, the therapeutically effective amount of the composition is administered for at least five consecutive days. In some embodiments, the therapeutically effective amount of the composition is administered for at least seven consecutive days. In some embodiments, the therapeutically effective amount of the composition is administered at least for about 15 days, about 21 days, about 24 days, about 28 days, or about 30 days. In some embodiments, the therapeutically effective amount of the composition comprises from about 0.001% to about 0.04% of concentration. In some embodiments, the therapeutically effective amount of the composition comprises from about 0.005% to about 0.02% of concentration. In some embodiments, the therapeutically effective amount of the composition comprises from about 0.005% to about 0.04% of concentration. In some embodiments, the therapeutically effective amount of the composition comprises from about 0.01% to about 0.02% of concentration.

In some embodiments, the administering comprises topical administration or transdermal administration. In some embodiments, the topical administration comprises administration of the composition to an affected skin area. In some embodiments, the topical administration comprises administering an ointment, cream, suspensions, paste, lotions, powders, solutions, oils, encapsulated gel, liposomes, sprayable aerosol or vapors, or any combination thereof.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
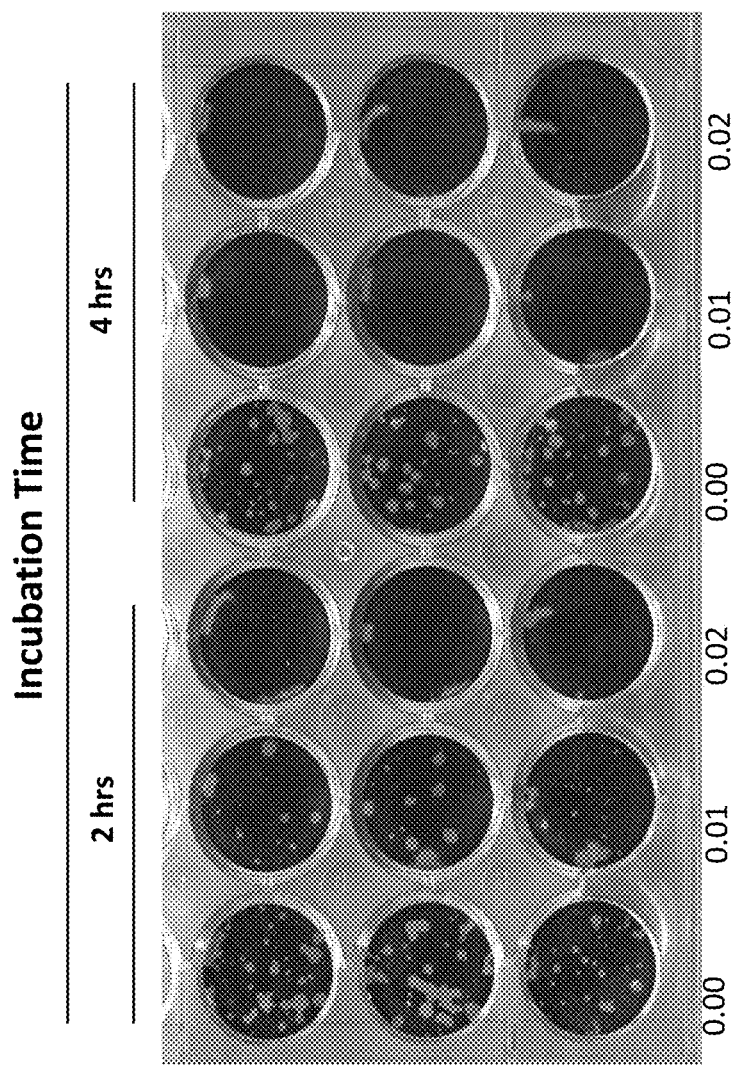
FIGS. 1A and 1B show results of plaque assay after incubations of HSV-1 with various concentrations of thujopsene for 2 or 4 hours.

Over-growth of microorganisms (microbes) including bacteria, viruses, fungi, and parasites may cause infections in human body. The microbes are categorized into more than a trillion species, but only a small number cause infection in humans. These are called pathogens. Skin diseases also can be caused by viruses, bacteria, fungi, or parasites. The most common bacterial skin pathogens are *Staphylococcus aureus* and group A (3-hemolytic streptococci. Herpes simplex is the most common viral skin disease. The high degree of infectiousness and fast reproduction cycle of viruses within host organisms make viruses a nuisance and a health hazard. There is no simple treatment of viral diseases. Viruses are not susceptible to antibiotics.

Viruses and Bacteria

Herpes Simplex is an enveloped double-stranded DNA virus that is responsible for primary and recurrent infections in humans and causes contagious sores, most often around the mouth or on the genitals. Symptoms of Herpes Simplex Virus (HSV) infections include an eruption of tiny blisters on the skin or mucous membranes. The virus remains in a dormant state inside the group of nerve cells that supply the nerve fibers to the infected area. The virus reactivates, begins growing again, and travels through the nerve fibers back to the skin, thereby causing eruption of blisters in the same area of skin as the earlier infection. HSV is classified into two types, HSV-1 and HSV-2. HSV has been known to contribute to a variety of disorders. HSV-1 is the common cause of adult encephalitis. A person infected with HSV-1 will always be a carrier of the virus. It is important to diagnose HSV infection at an early stage. HSV-1 commonly causes herpes labialism located on a lip, and keratitis, an inflammation of the cornea. Herpes simplex virus is very infectious and is rapidly and easily transferable by contact. There is no specific therapy for this extremely painful viral infection. Current treatment of HSV infections is limited primarily to systemic administration of the above-mentioned antiviral drugs with corresponding adverse side effects.

Vaccinia virus (VACV or VV) is a large, complex, enveloped virus belonging to the poxvirus family. The exact origins of vaccinia virus are uncertain and vaccinia may represent a hybrid of the variola (small pox) and cowpox viruses. Inoculation with vaccina virus produces a localized skin infection. Vaccinia can be spread by touching the vaccination site before it has fully healed or by touching clothing or bandages that have been contaminated with the live virus during vaccination. Vaccinia virus symptoms are similar to smallpox, but milder. Vaccinia may cause rash, fever, headache and body aches. Inoculation with vaccina virus produces a localized skin infection.

Coronaviruses are enveloped, positive-sense RNA viruses that infect mammalian and avian species. Human coronaviruses (HCoVs) are classified into groups 1 and 2, differentiated in sequence and antigenicity. Two HCoVs species (229E and OC43) have been known about a long time to cause mild respiratory infections. Coronavirus (229E-VR740) have been implicated in causing mild respiratory disease and, after rhinoviruses, are a leading cause of common colds. It is known as one of four endemic human coronavirus (CoVs) including NL63, HKU1, OC43-CoV (OC43), and 229E-CoV (229E), in addition to recently emerged zoonotic corona viruses severe acute respiratory syndrome coronavirus 1 (SARS-CoV-1), Middle East respiratory syndrome (MERS)-CoV, and SARS-CoV-2. HCoV were first isolated in the mid-1960s from patients with upper respiratory tract disease. The identification of coronaviruses in clinical samples was a very difficult task until the 1970s, as HCoV induced subtle or nonexistent cytopathic effects, and many cell types were not susceptible to the virus.

*Staphylococcus aureus* (staph) is a type of bacteria found on people's skin. Staph bacteria are usually harmless, but they can cause serious infections that can lead to sepsis or death. Once the staph germ enters the body, it can spread to bones, joints, the blood, or any organ, such as the lungs, heart, or brain. Serious staph infections are more common in people with chronic (long-term) medical problems. Methicillin-sensitive *Staphylococcus aureus* (MSSA) is a skin infection that is not resistant to certain antibiotics. MSSA normally presents as pimples, boils, abscesses or infected cuts, but also may cause pneumonia and other serious skin infections. MSSA affects people of all ages and colonizes the skin, causing no symptoms and without causing infection, but then may later lead to infection. The infection spreads via direct skin-to-skin contact and also may spread via contact with contaminated items or surfaces. Although antibiotics are used to treat MSSA infection, not all MSSA infections require antibiotics as the drainage of small abscesses may be all that is required. Early diagnosis and treatment may reduce the chance of developing severe infection. Methicillin-Resistant *S. aureus* (MRSA) is a bacterium that causes infections in different parts of the body. The symptoms of MRSA depend on the site is infected. Most often, it causes mild infections on the skin, like sores, boils, or abscesses. But it can also cause more serious skin infections or infect surgical wounds, the bloodstream, the lungs, or the urinary tract.

*Streptococcus dysgalactiae* is a gram-positive, beta-haemolytic, coccal bacterium. It has two subspecies including *S. dysgalactiae* subsp. *Dysgalactiae* (SDSD) and *S. dysgalactiae* subsp. *Equisimilis* (SDSE). Among them, SDSE has been known as an increasingly important human pathogen, causing a variety of superficial, deep, toxin-mediated, or immunologically mediated diseases in humans. Pharyngitis is a classic presentation in adult patients. SDSE also presents as skin and soft-tissue infections, including pyoderma, cellulitis, wound infections, abscesses, erysipelas, and necrotizing fasciitis. Invasive infections comprise arthritis, osteomyelitis, pleuropulmonary infections, peritonitis, intraabdominal and epidural abscesses, meningitis, endocarditis, puerperal septicemia, neonatal infections, necrotizing fasciitis, myositis, and streptococcal toxic-like syndrome.

*Streptococcus pyogenes* (*S. pyogenes*) is a facultative, gram-positive coccus which grows in chains and causes numerous infections in humans including pharyngitis, tonsillitis, scarlet fever, cellulitis, erysipelas, rheumatic fever, post-streptococcal glomerulonephritis, necrotizing fasciitis, myonecrosis and lymphangitis. The only known reservoirs for this in nature are the skin and mucous membranes of the human host. It can cause both noninvasive and invasive disease, as well as nonsuppurative sequelae. A ubiquitous organism, *S pyogenes* is the most common bacterial cause of acute pharyngitis, accounting for 15-30% of cases in children and 5-10% of cases in adults. The increased number and severity of *S. pyogenes* infections present special challenges to both the general practitioner and the infectious disease specialist, and the treatment of *S. pyogenes* infections has taken on greater importance.

Disclosed herein are a pharmaceutical composition and a method to treat microbial infections. In some embodiments, the pharmaceutical composition disclosed herein comprises at least about 10 v/v % of thujopsene. In another embodiments, the pharmaceutical composition disclosed herein comprises at least about 10 v/v % of thujopsene and at least about 10 v/v % of totarol. Thujopsene is a natural chemical compound, classified as a sesquiterpene, with the molecular formula $C_{15}H_{24}$. Thujopsene is found in the essential oil of a variety of conifers. Totarol is a naturally produced diterpene that is bioactive. The chemical formula of totarol is $C_{20}H_{30}O$.

Compositions

The present disclosure provides a pharmaceutical composition for treating a viral infection in a subject in need thereof. In some embodiments, the composition comprises at least about 10% of thujopsene. In some embodiments, the viral infection is caused by a herpesvirus (HSV). Examples of the HSV include, but not limited to HSV-1, HSV-2, varicella-zoster virus (VZV), Epstein-Barr virus (EBV), human cytomegalovirus (HCMV), human herpesvirus 6A (HHV-6A), human herpesvirus 6B (HHV-6B), human herpesvirus 7 (HHV-7), or Kaposi's sarcoma-associated herpesvirus (KSHV). In some embodiments, the viral infection is caused by a poxvirus. Examples of the poxvirus include, but not limited to smallpox virus (variola), vaccinia virus, cowpox virus, monkeypox virus, orf virus, pseudocowpox virus, bovine popular stomatitis virus, tanapox virus, yaba monkey tumor virus, or molluscum contagiosum virus. In some embodiments, the viral infection is caused by a coronavirus. Examples of the coronavirus include, but not limited to 229E, NL63, OC43, HKU1, MERS-CoV, SARS-CoV, SARS-CoV-2, or a variant thereof. In some embodiments, the composition optionally further comprises at least one pharmaceutically acceptable carrier, at least one diluent, at least one excipient or at least one additive.

The pharmaceutical composition disclosed herein comprises about 10%, about 20%, about 30%, about 40%, about 50%, about 60%, about 70%, about 80%, about 90%, or about 100% of thujopsene. In some embodiments, the composition comprises at least about 10%, about 20%, about 30%, about 40%, about 50%, about 60%, about 70%, about 80%, about 90%, or about 100% of thujopsene. In some embodiments, the composition comprises at most about 10%, about 20%, about 30%, about 40%, about 50%, about 60%, about 70%, about 80%, about 90%, or about 100% of thujopsene. In some embodiments, the composition comprises from about 10% to about 100%, from about 20% to about 90%, from about 30% to about 80%, from about 40% to about 70%, or from about 50% to about 60% of thujopsene.

A purity of the thujopsene is determined by high-performance liquid chromatography (HPLC). In some cases, HPLC purification is performed as a normal-phase chromatography. In some cases, HPLC purification is performed as a reverse-phase chromatography. In some embodiments, the thujopsene has a purity of about 80%, about 82%, about 84%, about 86%, about 88%, about 90%, about 92%, about 94%, about 95%, or about 100%. In some embodiments, the thujopsene has a purity of at least about 80%, about 82%, about 84%, about 86%, about 88%, about 90%, about 92%, about 94%, about 95%, or about 100%. In some embodiments, the thujopsene has a purity of at most about 80%, about 82%, about 84%, about 86%, about 88%, about 90%, about 92%, about 94%, about 95%, about 100%. In some embodiments, the thujopsene has a purity of from about 80% to about 100%, from about 82% to about 95%, from about 84% to about 94%, from about 86% to about 92%, or from about 88% to about 90%. In some embodiments, the thujopsene has a purity of about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

The pharmaceutical composition disclosed herein optionally further comprises at least one pharmaceutically acceptable carrier, at least one diluent, at least one excipient or at least one additive. Non-limiting examples of the at least one pharmaceutically acceptable carrier comprises dimethyl sulfoxide (DMSO), alpha-thujene, alpha-pinene, camphene, sabinene, beta-pinene, alpha-terpinene, benzene, limonene, peltay2-carene, trans sabinene hydrate, terpinolene, 3-cyclohexen-1-ol, terpinene-4-ol, 1,2-benzenediol, linalyl acetae, borneol, bornyl acetate, alph-thujone, terpinyl acetate, iso-longifolene, epit-bicyclosesquiphellandrene, alpha-humulene, guaiol, elemol, cedrol, beta-eudesmol, rosifoliol, rimuene, hexadecanoic acid, cembrene, verticellol, totarol, totara-1,9-octadecenamide, tatarol, 2-(hexylthiol)decanal, and combinations thereof.

In some embodiments, the concentration of the DMSO is about 0.05%, about 0.075%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 20%, about 30%, about 40%, about 50%, about 60%, about 70%, about 80%, or about 90%. In some embodiments, the concentration of DMSO is at least about 0.05%, about 0.075%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 20%, about 30%, about 40%, about 50%, about 60%, about 70%, about 80%, or about 90%. In some embodiments, the concentration of DMSO is at most about 0.05%, about 0.075%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 20%, about 30%, about 40%, about 50%, about 60%, about 70%, about 80%, or about 90%. In some embodiments, concentration of the DMSO is from about 0.05% to about 90%, from about 0.075% to about 80%, from about 0.1% to about 70%, from about 0.2% to about 60%, from about 0.3% to about 50%, from about 0.4% to about 40%, from about 0.5% to about 30%, from about 0.6% to about 20%, from about 0.7% to about 10%, from about 0.4% to about 40%, from about 0.5% to about 30%, from about 0.6% to about 20%, from about 0.7% to about 10%, from about 0.8% to about 9%, from about 0.9% to about 8%, from about 1% to about 7%, from about 2% to about 6%, from about 3% to about 5%, or from about 4% to about 90%.

In some embodiments, the at least one diluent comprises gentamicin/amphotericin. In some embodiments, the concentration of the gentamicin/amphotericin is about 0.2%, about 0.4%, about 0.6%, about 0.8%, about 1%, about 1.2%, about 1.4%, about 1.6%, about 1.8%, about 2%, about 3%, about 4%, about 5%, about 6%, about 7%, about 8%, about 9%, about 10%, about 20%, about 30%, about 40%, about 50%, about 60%, about 70%, about 80%, or about 90%. In some embodiments, the concentration of the gentamicin/amphotericin is at least about 0.2%, about 0.4%, about 0.6%, about 0.8%, about 1%, about 1.2%, about 1.4%, about 1.6%, about 1.8%, about 2%, about 3%, about 4%, about 5%, about 6%, about 7%, about 8%, about 9%, about 10%, about 20%, about 30%, about 40%, about 50%, about 60%, about 70%, about 80%, or about 90%. In some embodiments, the concentration of the gentamicin/amphotericin is at most about 0.2%, about 0.4%, about 0.6%, about 0.8%, about 1%, about 1.2%, about 1.4%, about 1.6%, about 1.8%, about 2%, about 3%, about 4%, about 5%, about 6%, about 7%, about 8%, about 9%, about 10%, about 20%, about 30%, about 40%, about 50%, about 60%, about 70%, about 80%, or about 90%. In some embodiments, the concentration of the gentamicin/amphotericin is from about 0.2% to about 90%, from about 0.3% to about 80%, from about 0.4% to about 70%, from about 0.5% to about 60%, from about 0.6% to about 50%, from about 0.7% to about 40%, from about 0.4% to about 30%, from about 0.5% to about 20%, from about 0.6% to about 10%, from about 0.7% to about 9%, from about 0.8% to about 8%, from about 0.9% to about 7%, from about 1% to about 6%, from about 2% to about 5%, or from about 3% to about 4%. Non-limiting examples of the at least one diluent are buffer, saline, water, DMSO, or combinations thereof.

The pharmaceutical composition disclosed herein optionally further comprises at least one pharmaceutically acceptable excipient. In some embodiments, the at least one excipient is selected from the group consisting of: animal and vegetable fats, oils, waxes, paraffins, starch, tragacanth, cellulose derivatives, polyethylene glycols, silicones, bentonites, silicic acid, talc, zinc oxide, lactose, talc, silicic acid, aluminum hydroxide, calcium silicates, polyamide powder, and combinations thereof. In some embodiments, the at least one excipient is naturally occurring. In another embodiments, at least one excipient is non-naturally occurring.

The pharmaceutical composition disclosed herein optionally further comprises at least one pharmaceutically acceptable additives. Non-limiting examples of the at least one additive comprise a fatty substance, an organic solvent, a solubilizing agent, a thickener, a gelling agent, a softener, an antioxidant, a suspending agent, a stabilizer, a foaming agent, an aromatic, a surfactant, water, an ionic or non-ionic emulsifying agent, a filler, a sequestering agent, a chelating agent, a preservative, vitamins, a blocker, a moisturizing agent, essential oil, a dye, a pigment, a hydrophilic or hydrophobic activator, a lipid vesicle, antiseptics, stabilizing agents, hydrating agents, emulsification promoters or salts and/or buffers for osmotic control, and combinations thereof. In some embodiments, the at least one additive is naturally occurring. In another embodiments, at least one additive is non-naturally occurring. In some embodiments, the at least one additive comprises other therapeutically useful substances. In additional embodiments, the at least one additive further comprises absorption enhancers, permeation enhancers, thickening agents, viscosity enhancers, agents for adjusting and/or maintaining the pH, agents to adjust the osmotic pressure, preservatives, surfactants, buffers, salts (preferably sodium chloride), suspending agents, dispersing agents, solubilizing agents, stabilizers and/or tonicity agents.

The present disclosure also provides a pharmaceutical composition for treating a microbial infection in a subject in need thereof. In some embodiments, the composition comprises at least about 10% of thujopsene and at least about 10% of totarol. In some embodiments, the microbial infection comprises a bacterial infection. In some embodiments, the bacterial infection is caused by *Staphylococcus aureus*. In some embodiments, the bacterial infection is caused by methicillin-resistant staph (MRSA), methicillin-susceptible staph (MSSA), or a combination thereof. In some embodiments, the bacterial infection is caused by *Streptococcus*. In some embodiments, the bacterial infection is caused by

*Streptococcus pyogenes, Streptococcus dysgalactiae, Streptococcus anginosus*, or a combination thereof.

The pharmaceutical composition disclosed herein comprises about 10%, about 20%, about 30%, about 40%, about 50%, about 60%, about 70%, about 80%, about 90%, or about 100% of thujopsene. In some embodiments, the composition comprises at least about 10%, about 20%, about 30%, about 40%, about 50%, about 60%, about 70%, about 80%, about 90%, or about 100% of thujopsene. In some embodiments, the composition comprises at most about 10%, about 20%, about 30%, about 40%, about 50%, about 60%, about 70%, about 80%, about 90%, or about 100% of thujopsene. In some embodiments, the composition comprises from about 10% to about 100%, from about 20% to about 90%, from about 30% to about 80%, from about 40% to about 70%, or from about 50% to about 60% of thujopsene.

The pharmaceutical composition disclosed herein comprises about 10%, about 20%, about 30%, about 40%, about 50%, about 60%, about 70%, about 80%, about 90%, or about 100% of totarol. In some embodiments, the composition comprises at least about 10%, about 20%, about 30%, about 40%, about 50%, about 60%, about 70%, about 80%, about 90%, or about 100% of totarol. In some embodiments, the composition comprises at most about 10%, about 20%, about 30%, about 40%, about 50%, about 60%, about 70%, about 80%, about 90%, or about 100% of totarol. In some embodiments, the composition comprises from about 10% to about 100%, from about 20% to about 90%, from about 30% to about 80%, from about 40% to about 70%, or from about 50% to about 60% of totarol.

A purity of the thujopsene is determined by HPLC. In some cases, HPLC purification is performed as a normal-phase chromatography. In some cases, HPLC purification is performed as a reverse-phase chromatography. In some embodiments, the thujopsene has a purity of about 80%, about 82%, about 84%, about 86%, about 88%, about 90%, about 92%, about 94%, about 95%, or about 100%. In some embodiments, the thujopsene has a purity of at least about 80%, about 82%, about 84%, about 86%, about 88%, about 90%, about 92%, about 94%, about 95%, or about 100%. In some embodiments, the thujopsene has a purity of at most about 80%, about 82%, about 84%, about 86%, about 88%, about 90%, about 92%, about 94%, about 95%, about 100%. In some embodiments, the thujopsene has a purity of from about 80% to about 100%, from about 82% to about 95%, from about 84% to about 94%, from about 86% to about 92%, or from about 88% to about 90%. In some embodiments, the thujopsene has a purity of about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

A purity of the totarol is determined by HPLC. In some cases, HPLC purification is performed as a normal-phase chromatography. In some cases, HPLC purification is performed as a reverse-phase chromatography. In some embodiments, the totarol has a purity of about 80%, about 82%, about 84%, about 86%, about 88%, about 90%, about 92%, about 94%, about 95%, or about 100%. In some embodiments, the totarol has a purity of at least about 80%, about 82%, about 84%, about 86%, about 88%, about 90%, about 92%, about 94%, about 95%, or about 100%. In some embodiments, the totarol has a purity of at most about 80%, about 82%, about 84%, about 86%, about 88%, about 90%, about 92%, about 94%, about 95%, about 100%. In some embodiments, the totarol has a purity of from about 80% to about 100%, from about 82% to about 95%, from about 84% to about 94%, from about 86% to about 92%, or from about 88% to about 90%. In some embodiments, the totarol has a purity of about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

The pharmaceutical composition disclosed herein optionally further comprises at least one pharmaceutically acceptable carrier, at least one diluent, at least one excipient or at least one additive. Non-limiting examples of the at least one pharmaceutically acceptable carrier comprises dimethyl sulfoxide (DMSO), alpha-thujene, alpha-pinene, camphene, sabinene, beta-pinene, alpha-terpinene, benzene, limonene, peltay2-carene, trans sabinene hydrate, terpinolene, 3-cyclohexen-1-ol, terpinene-4-ol, 1,2-benzenediol, linalyl acetae, borneol, bornyl acetate, alph-thujone, terpinyl acetate, isolongifolene, epit-bicyclosesquiphellandrene, alpha-humulene, guaiol, elemol, cedrol, beta-eudesmol, rosifoliol, rimuene, hexadecanoic acid, cembrene, verticellol, totarol, totara-1,9-octadecenamide, tatarol, 2-(hexylthiol)decanal, and combinations thereof.

In some embodiments, the concentration of the DMSO is about 0.05%, about 0.075%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 20%, about 30%, about 40%, about 50%, about 60%, about 70%, about 80%, or about 90%. In some embodiments, the concentration of DMSO is at least about 0.05%, about 0.075%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 20%, about 30%, about 40%, about 50%, about 60%, about 70%, about 80%, or about 90%. In some embodiments, the concentration of DMSO is at most about 0.05%, about 0.075%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 20%, about 30%, about 40%, about 50%, about 60%, about 70%, about 80%, or about 90%. In some embodiments, concentration of the DMSO is from about 0.05% to about 90%, from about 0.075% to about 80%, from about 0.1% to about 70%, from about 0.2% to about 60%, from about 0.3% to about 50%, from about 0.4% to about 40%, from about 0.5% to about 30%, from about 0.6% to about 20%, from about 0.7% to about 10%, from about 0.4% to about 40%, from about 0.5% to about 30%, from about 0.6% to about 20%, from about 0.7% to about 10%, from about 0.8% to about 9%, from about 0.9% to about 8%, from about 1% to about 7%, from about 2% to about 6%, from about 3% to about 5%, or from about 4% to about 90%.

In some embodiments, the at least one diluent comprises gentamicin/amphotericin. In some embodiments, concentration of the gentamicin/amphotericin is about 0.2%, about 0.4%, about 0.6%, about 0.8%, about 1%, about 1.2%, about 1.4%, about 1.6%, about 1.8%, about 2%, about 3%, about 4%, about 5%, about 6%, about 7%, about 8%, about 9%, about 10%, about 20%, about 30%, about 40%, about 50%, about 60%, about 70%, about 80%, or about 90%. In some embodiments, concentration of the gentamicin/amphotericin is at least about 0.2%, about 0.4%, about 0.6%, about 0.8%, about 1%, about 1.2%, about 1.4%, about 1.6%, about 1.8%, about 2%, about 3%, about 4%, about 5%, about 6%, about 7%, about 8%, about 9%, about 10%, about 20%, about 30%, about 40%, about 50%, about 60%, about 70%, about 80%, or about 90%. In some embodiments, concentration of the gentamicin/amphotericin is at most about 0.2%, about 0.4%, about 0.6%, about 0.8%, about 1%, about 1.2%, about 1.4%, about 1.6%, about 1.8%, about 2%, about 3%, about 4%, about 5%, about 6%, about 7%, about 8%, about 9%, about 10%, about 20%, about 30%, about 40%, about 50%, about 60%, about 70%, about 80%, or about 90%. In some embodiments, concentration of the gentamicin/amphotericin is from about 0.2% to about 90%, from about 0.3% to about 80%, from about 0.4% to about 70%, from about 0.5% to about 60%, from about 0.6% to about 50%, from about 0.7% to about 40%, from about 0.4% to about 30%, from about 0.5% to about 20%, from about 0.6% to about 10%, from about 0.7% to about 9%, from about 0.8% to about 8%, from about 0.9% to about 7%, from about 1% to about 6%, from about 2% to about 5%, or from about 3% to about 4%. Non-limiting examples of the at least one diluent are buffer, saline, water, DMSO, or combinations thereof.

The pharmaceutical composition disclosed herein optionally further comprises at least one pharmaceutically acceptable excipient. In some embodiments, the at least one excipient is selected from the group consisting of: animal and vegetable fats, oils, waxes, paraffins, starch, tragacanth, cellulose derivatives, polyethylene glycols, silicones, bentonites, silicic acid, talc, zinc oxide, lactose, talc, silicic acid, aluminum hydroxide, calcium silicates, polyamide powder, and combinations thereof. In some embodiments, the at least one excipient is naturally occurring. In another embodiments, at least one excipient is non-naturally occurring.

The pharmaceutical composition disclosed herein optionally further comprises at least one pharmaceutically acceptable additives. Non-limiting examples of the at least one additive comprise a fatty substance, an organic solvent, a solubilizing agent, a thickener, a gelling agent, a softener, an antioxidant, a suspending agent, a stabilizer, a foaming agent, an aromatic, a surfactant, water, an ionic or non-ionic emulsifying agent, a filler, a sequestering agent, a chelating agent, a preservative, vitamins, a blocker, a moisturizing agent, essential oil, a dye, a pigment, a hydrophilic or hydrophobic activator, a lipid vesicle, antiseptics, stabilizing agents, hydrating agents, emulsification promoters or salts and/or buffers for osmotic control, and combinations thereof. In some embodiments, the at least one additive is naturally occurring. In another embodiments, at least one additive is non-naturally occurring. In some embodiments, the at least one additive comprises other therapeutically useful substances. In additional embodiments, the at least one additive further comprises absorption enhancers, permeation enhancers, thickening agents, viscosity enhancers, agents for adjusting and/or maintaining the pH, agents to adjust the osmotic pressure, preservatives, surfactants, buffers, salts (preferably sodium chloride), suspending agents, dispersing agents, solubilizing agents, stabilizers and/or tonicity agents.

Methods

The present disclosure also provides a method for treating a viral infection in a subject in need thereof by administering to the subject a therapeutically effective amount of a composition. In some embodiments, the composition is administered to the subject by a route selected from the group consisting of intranasal, inhalational, topical, oral, peritoneal, parenteral, intramuscular, subcutaneous, transdermal, epidural, intratracheal, otic, intraocular, intrathecal, and intravenous. In some embodiments, the composition comprises at least about 10 v/v % of thujopsene. In some embodiments, the composition comprises about 10 v/v %, about 20 v/v %, about 30 v/v %, about 40 v/v %, about 50 v/v %, about 60 v/v %, about 70 v/v %, about 80 v/v %, about 90 v/v %, or 100 v/v % of thujopsene. In some embodiments, the composition comprises at least about 10 v/v %, about 20 v/v %, about 30 v/v %, about 40 v/v %, about 50 v/v %, about 60 v/v %, about 70 v/v %, about 80 v/v %, about 90 v/v %, or about 100 v/v % of thujopsene. In some embodiments, the composition comprises at most about 10 v/v %, about 20 v/v %, about 30 v/v %, about 40 v/v %, about 50 v/v %, about 60 v/v %, about 70 v/v %, about 80 v/v %, about 90 v/v %, or about 100 v/v % of thujopsene. In some embodiments, the composition comprises from about 10 v/v % to about 100 v/v %, from about 20 v/v % to about 90 v/v %, from about 30 v/v % to about 80 v/v %, from about 40 v/v % to about 70 v/v %, or from about 50 v/v % to about 60 v/v % of thujopsene.

In another embodiments, the composition for topical administration is formulated as a liquid or semi-solid material, such as a gel, paste, putty, ointment, cream, emulsion, patch, etc. as well as other biocompatible materials or polymers. In some embodiments, the composition for topical administration is formulated as a dry or solid preparation, such as powders, granules, etc., that are applied directly to a desired site of action. According to some embodiments, the composition for topical administration is molded into a desired size and shape, such as for placement within or to fill a space at a desired site of administration in the body of an individual, subject, or patient. In some embodiments, the composition described herein is topically administered at two or more sites. In some embodiments, the composition comprises at least about 10% of thujopsene. In some embodiments, the composition comprises about 10 w/w %, about 20 w/w %, about 30 w/w %, about 40 w/w %, about 50 w/w %, about 60 w/w %, about 70 w/w %, about 80 w/w %, about 90 w/w %, or 100 w/w % of thujopsene. In some embodiments, the composition comprises at least about 10 w/w %, about 20 w/w %, about 30 w/w %, about 40 w/w %, about 50 w/w %, about 60 w/w %, about 70 w/w %, about 80 w/w %, about 90 w/w %, or about 100 w/w % of thujopsene. In some embodiments, the composition comprises at most about 10 w/w %, about 20 w/w %, about 30 w/w %, about 40 w/w %, about 50 w/w %, about 60 w/w %, about 70 w/w %, about 80 w/w %, about 90 w/w %, or about 100 w/w % of thujopsene. In some embodiments, the composition comprises from about 10 w/w % to about 100 w/w %, from about 20 w/w % to about 90 w/w %, from about 30 w/w % to about 80 w/w %, from about 40 w/w % to about 70 w/w %, or from about 50 w/w % to about 60 w/w % of thujopsene.

A purity of the thujopsene is determined by HPLC. In some cases, HPLC purification is performed as a normal-phase chromatography. In some cases, HPLC purification is performed as a reverse-phase chromatography. In some embodiments, the thujopsene has a purity of about 80%, about 82%, about 84%, about 86%, about 88%, about 90%, about 92%, about 94%, about 95%, or about 100%. In some embodiments, the thujopsene has a purity of at least about 80%, about 82%, about 84%, about 86%, about 88%, about 90%, about 92%, about 94%, about 95%, or about 100%. In some embodiments, the thujopsene has a purity of at most about 80%, about 82%, about 84%, about 86%, about 88%, about 90%, about 92%, about 94%, about 95%, or about 100%. In some embodiments, the thujopsene has a purity of from about 80% to about 100%, from about 82% to about 95%, from about 84% to about 94%, from about 86% to about 92%, or from about 88% to about 90%.

In some embodiments, the viral infection is caused by a herpesvirus (HSV). In some embodiments, the HSV comprises HSV-1, HSV-2, varicella-zoster virus (VZV), Epstein-Barr virus (EBV), human cytomegalovirus (HCMV), human herpesvirus 6A (HHV-6A), human herpesvirus 6B (HHV-6B), human herpesvirus 7 (HHV-7), or Kaposi's sarcoma-associated herpesvirus (KSHV). In some embodiments, the viral infection is caused by a poxvirus. In some embodiments, the poxvirus comprises smallpox virus (variola), vaccinia virus, cowpox virus, monkeypox virus, orf virus, pseudocowpox virus, bovine popular stomatitis virus, tanapox virus, yaba monkey tumor virus, or molluscum contagiosum virus. In some embodiments, the viral infection is caused by a coronavirus. In some embodiments, the coronavirus comprises 229E, NL63, OC43, or HKU1. In some embodiments, the coronavirus comprises MERS-CoV, SARS-CoV, SARS-CoV-2, or a variant thereof.

In some embodiments, administering the composition decreases or reduces viral titer in the subject. In some embodiments, the viral titer in the subject is measured by determining the number of plaque forming units (pfu) in a cell in the subject. In some embodiments, the viral titer in the subject is decreased or reduced by at least about 10%, 20%, 30%, 40%, 50%, 60%, 70%, 80%, or 90% within 2 hours after the administration. In some embodiments, the viral titer in the subject is decreased or reduced by at most about 10%, 20%, 30%, 40%, 50%, 60%, 70%, 80%, or 90% within 2 hours after the administration. In some embodiments, the viral titer in the subject is decreased or reduced by about 10% to about 90%, about 20% to about 80%, about 30% to about 70%, about 40% to about 60%, or about 50% to 90% within 2 hours after the administration. In some embodiments, the viral titer in the subject is decreased or reduced by at least about 10%, 20%, 30%, 40%, 50%, 60%, 70%, 80%, or 90% within 4 hours after the administration. In some embodiments, the viral titer in the subject is decreased or reduced by at most about 10%, 20%, 30%, 40%, 50%, 60%, 70%, 80%, or 90% within 4 hours after the administration. In some embodiments, the viral titer in the subject is decreased or reduced by about 10% to about 90%, about 20% to about 80%, about 30% to about 70%, about 40% to about 60%, or about 50% to 90% within 4 hours after the administration.

In some embodiments, the composition decreases or reduces the activity of viruses in the subject. In some embodiments, the activity of viruses in the subject is decreased or reduced by at least about 10%, 20%, 30%, 40%, 50%, 60%, 70%, 80%, or 90% within 2 hours after the administration. In some embodiments, the activity of viruses in the subject is decreased or reduced by at most about 10%, 20%, 30%, 40%, 50%, 60%, 70%, 80%, or 90% within 2 hours after the administration. In some embodiments, the activity of viruses in the subject is decreased or reduced by about 10% to about 90%, about 20% to about 80%, about 30% to about 70%, about 40% to about 60%, or about 50% to 90% within 2 hours after the administration. In some embodiments, the activity of viruses in the subject is decreased or reduced by at least about 10%, 20%, 30%, 40%, 50%, 60%, 70%, 80%, or 90% within 4 hours after the administration. In some embodiments, the activity of viruses in the subject is decreased or reduced by at most about 10%, 20%, 30%, 40%, 50%, 60%, 70%, 80%, or 90% within 4 hours after the administration. In some embodiments, the activity of viruses in the subject is decreased or reduced by about 10% to about 90%, about 20% to about 80%, about 30% to about 70%, about 40% to about 60%, or about 50% to 90% within 4 hours after the administration.

In some embodiments, the composition decreases or reduces viral gene expression in the subject. In some embodiments, the gene expression of viruses in the subject is decreased or reduced by at least about 10%, 20%, 30%, 40%, 50%, 60%, 70%, 80%, or 90% within 2 hours after the administration. In some embodiments, the gene expression of viruses in the subject is decreased or reduced by at mot about 10%, 20%, 30%, 40%, 50%, 60%, 70%, 80%, or 90% within 2 hours after the administration. In some embodiments, the gene expression of viruses in the subject is decreased or reduced by about 10% to about 90%, about 20% to about 80%, about 30% to about 70%, about 40% to about 60%, or about 50% to 90% within 2 hours after the administration. In some embodiments, the gene expression of viruses in the subject is decreased or reduced by at least about 10%, 20%, 30%, 40%, 50%, 60%, 70%, 80%, or 90% within 4 hours after the administration. In some embodiments, the gene expression of viruses in the subject is decreased or reduced by at most about 10%, 20%, 30%, 40%, 50%, 60%, 70%, 80%, or 90% within 4 hours after the administration. In some embodiments, the gene expression of viruses in the subject is decreased or reduced by about 10% to about 90%, about 20% to about 80%, about 30% to about 70%, about 40% to about 60%, or about 50% to 90% within 4 hours after the administration.

In some embodiments, the composition prevents, inhibits, or slows the destruction of a cell in the subject. In some embodiments, the cell comprises fibroblast. In some embodiments, the therapeutically effective amount of the composition is administered one to five times a day. In some embodiments, the therapeutically effective amount of the composition is administered one, twice, three times, four times or five times a day. In some embodiments, the therapeutically effective amount of the composition is administered one to five times, twice to four times, or three times to five times a day. In some embodiments, the therapeutically effective amount of the composition is administered for at least five consecutive days. In some embodiments, the therapeutically effective amount of the composition is administered for at least six consecutive days. In some embodiments, the therapeutically effective amount of the composition is administered for at least seven consecutive days. In some embodiments, the therapeutically effective amount of the composition is administered for at least five, at least six, or at least seven consecutive days. In some embodiments, the therapeutically effective amount of the composition is administered for at most five, at least six, or at least seven consecutive days. In some embodiments, the therapeutically effective amount of the composition is administered for from five to seven consecutive days. In some embodiments, the therapeutically effective amount of the composition is administered about 15 days, about 21 days, about 24 days, about 28 days, or about 30 days. In some embodiments, the therapeutically effective amount of the composition is administered at most for about 15 days, about 21 days, about 24 days, about 28 days, or about 30 days. In some embodiments, the therapeutically effective amount of the composition is administered for from about 15 days to about 30 days, from about 21 days to about 28 days, or from about 24 days to about 30 days. In some embodiments, the therapeutically effective amount of the composition is administered for from at least about 1 week, at least about 2 weeks, at least about 4 weeks, at least about 2 months, at least about 4 months, or at least about 6 months.

In some embodiments, the therapeutically effective amount of the composition ranges from about 0.001% to about 0.04% of concentration. In some embodiments, the therapeutically effective amount of the composition comprises from about 0.005% to about 0.02% of concentration. In some embodiments, the therapeutically effective amount of the composition comprises from about 0.005% to about 0.04% of concentration. In some embodiments, the therapeutically effective amount of the composition comprises from about 0.01% to about 0.02% of concentration. In some embodiments, the therapeutically effective amount of the composition comprises about 0.001%, about 0.005%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 20%, about 25%, about 30%, about 35%, about 40%, about 45%, or about 50% of concentration. In some embodiments, the therapeutically effective amount of the composition comprises at least about 0.001%, about 0.005%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 20%, about 25%, about 30%, about 35%, about 40%, about 45%, or about 50% of concentration. In some embodiments, the therapeutically effective amount of the composition comprises at most about 0.001%, about 0.005%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 20%, about 25%, about 30%, about 35%, about 40%, about 45%, or about 50% of concentration. In some embodiments, the therapeutically effective amount of the composition comprises from about 0.001% to about 50%, from about 0.005% to about 45%, from about 0.01% to about 40%, from about 0.015% to about 35%, from about 0.02% to about 30%, from about 0.03% to about 25%, from about 0.04% to about 20%, from about 0.05% to about 15%, from about 0.06% to about 14%, from about 0.07% to about 13%, from about 0.08% to about 12%, from about 0.09% to about 11%, from about 0.1% to about 10%, from about 0.2% to about 9%, from about 0.3% to about 8%, from about 0.4% to about 7%, from about 0.5% to about 6%, from about 0.6% to about 5%, from about 0.7% to about 4%, from about 0.8% to about 3%, from about 0.9% to about 2%, or from about 1% to about 50% of concentration. In some embodiments, the therapeutically effective amount of the composition comprises about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 5.0 mg/day, or 10 mg/day. In some embodiments, the therapeutically effective amount of the composition comprises at least about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 5.0 mg/day, or 10 mg/day. In some embodiments, the therapeutically effective amount of the composition comprises at most about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 5.0 mg/day, or 10 mg/day. In some embodiments, the therapeutically effective amount of the composition ranges from about 0.1 mg/day to about 10 mg/day, from about 0.2 mg/day to about 5.0 mg/day, from about 0.3 mg/day to about 1.0 mg/day, from about 0.4 mg/day to about 0.9 mg/day, from about 0.5 mg/day to about 0.8 mg/day, or from about 0.6 mg/day to about 0.7 mg/day.

The therapeutically effective amount of the composition disclosed herein can be administered via topical, transdermal, oral, or nasal administration routes. In some embodiments, the topical administration comprises administration of the composition to an affected skin area. Non-limiting examples of dosage forms for topical administration or for transdermal administration of the composition disclosed herein comprise an ointment, cream, suspensions, paste, lotions, powders, solutions, oils, encapsulated gel, liposomes, sprayable aerosol or vapors, solutions, patches, drops, inhalants, or combinations thereof. In some embodiments, sprayable aerosol or vapors additionally comprise customary propellants, for example chlorofluoro-hydrocarbons, and volatile unsubstituted hydrocarbons, for example butane and propane. In another embodiments, transdermal patches may provide an advantage of controlled delivery of the composition disclosed herein to the subject in need thereof. In some embodiments, the dosage forms are made by dissolving, dispersing or otherwise incorporating the composition disclosed herein in a proper medium. In some embodiments, absorption enhancers are also used to increase the flux of the composition across the skin. In some embodiments, the rate of the flux is controlled by either providing a rate-controlling membrane or dispersing the compound in a polymer matrix or gel. In some embodiments, a drug-impregnated solid carrier (e.g., a dressing) can also be used for topical administration and can be non-naturally occurring.

In another aspects, the present disclosure provides a method for a microbial infection in a subject in need thereof, comprising administering to the subject a therapeutically effective amount of a composition comprising thujopsene and totarol. In some embodiments, the composition comprises at least about 10% of thujopsene and at least about 10% of totarol.

In some embodiments, the composition is administered to the subject by a route selected from the group consisting of intranasal, inhalational, topical, oral, peritoneal, parenteral, intramuscular, subcutaneous, transdermal, epidural, intratracheal, otic, intraocular, intrathecal, and intravenous. In some embodiments, the composition comprises at least about 10 v/v % of thujopsene. In some embodiments, the composition comprises about 10 v/v %, about 20 v/v %, about 30 v/v %, about 40 v/v %, about 50 v/v %, about 60 v/v %, about 70 v/v %, about 80 v/v %, about 90 v/v %, or 100 v/v % of thujopsene. In some embodiments, the composition comprises at least about 10 v/v %, about 20 v/v %, about 30 v/v %, about 40 v/v %, about 50 v/v %, about 60 v/v %, about 70 v/v %, about 80 v/v %, about 90 v/v %, or about 100 v/v % of thujopsene. In some embodiments, the composition comprises at most about 10 v/v %, about 20 v/v %, about 30 v/v %, about 40 v/v %, about 50 v/v %, about 60 v/v %, about 70 v/v %, about 80 v/v %, about 90 v/v %, or about 100 v/v % of thujopsene. In some embodiments, the composition comprises from about 10 v/v % to about 100 v/v %, from about 20 v/v % to about 90 v/v %, from about 30 v/v % to about 80 v/v %, from about 40 v/v % to about 70 v/v %, or from about 50 v/v % to about 60 v/v % of thujopsene.

In some embodiments, the composition comprises at least about 10 v/v % of totarol. In some embodiments, the composition comprises about 10 v/v %, about 20 v/v %, about 30 v/v %, about 40 v/v %, about 50 v/v %, about 60 v/v %, about 70 v/v %, about 80 v/v %, about 90 v/v %, or 100 v/v % of totarol. In some embodiments, the composition comprises at least about 10 v/v %, about 20 v/v %, about 30 v/v %, about 40 v/v %, about 50 v/v %, about 60 v/v %, about 70 v/v %, about 80 v/v %, about 90 v/v %, or about 100 v/v % of totarol. In some embodiments, the composition comprises at most about 10 v/v %, about 20 v/v %, about 30 v/v %, about 40 v/v %, about 50 v/v %, about 60 v/v %, about 70 v/v %, about 80 v/v %, about 90 v/v %, or about 100 v/v % of totarol. In some embodiments, the composition comprises from about 10 v/v % to about 100 v/v %, from about 20 v/v % to about 90 v/v %, from about 30 v/v % to about 80 v/v %, from about 40 v/v % to about 70 v/v %, or from about 50 v/v % to about 60 v/v % of totarol.

In another embodiments, the composition for topical administration is formulated as a liquid or semi-solid material, such as a gel, paste, putty, ointment, cream, emulsion, patch, etc. as well as other biocompatible materials or polymers. In some embodiments, the composition for topical administration is formulated as a dry or solid preparation, such as powders, granules, etc., that are applied directly to a desired site of action. According to some embodiments, the composition for topical administration is molded into a desired size and shape, such as for placement within or to fill a space at a desired site of administration in the body of an individual, subject, or patient. In some embodiments, the composition described herein is topically administered at two or more sites. In some embodiments, the composition comprises at least about 10% of thujopsene. In some embodiments, the composition comprises about 10 w/w %, about 20 w/w %, about 30 w/w %, about 40 w/w %, about 50 w/w %, about 60 w/w %, about 70 w/w %, about 80 w/w %, about 90 w/w %, or 100 w/w % of thujopsene. In some embodiments, the composition comprises at least about 10 w/w %, about 20 w/w %, about 30 w/w %, about 40 w/w %, about 50 w/w %, about 60 w/w %, about 70 w/w %, about 80 w/w %, about 90 w/w %, or about 100 w/w % of thujopsene. In some embodiments, the composition comprises at most about 10 w/w %, about 20 w/w %, about 30 w/w %, about 40 w/w %, about 50 w/w %, about 60 w/w %, about 70 w/w %, about 80 w/w %, about 90 w/w %, or about 100 w/w % of thujopsene. In some embodiments, the composition comprises from about 10 w/w % to about 100 w/w %, from about 20 w/w % to about 90 w/w %, from about 30 w/w % to about 80 w/w %, from about 40 w/w % to about 70 w/w %, or from about 50 w/w % to about 60 w/w % of thujopsene. In some embodiments, the composition described herein is topically administered at two or more sites. In some embodiments, the composition comprises at least about 10 w/w % of totarol. In some embodiments, the composition comprises about 10 w/w %, about 20 w/w %, about 30 w/w %, about 40 w/w %, about 50 w/w %, about 60 w/w %, about 70 w/w %, about 80 w/w %, about 90 w/w %, or 100 w/w % of totarol. In some embodiments, the composition comprises at least about 10 w/w %, about 20 w/w %, about 30 w/w %, about 40 w/w %, about 50 w/w %, about 60 w/w %, about 70 w/w %, about 80 w/w %, about 90 w/w %, or 100 w/w % of totarol. In some embodiments, the composition comprises at most about 10 w/w %, about 20 w/w %, about 30 w/w %, about 40 w/w %, about 50 w/w %, about 60 w/w %, about 70 w/w %, about 80 w/w %, about 90 w/w %, or 100 w/w % of totarol. In some embodiments, the composition comprises from about 10 w/w % to about 100 w/w %, from about 20 w/w % to about 90 w/w %, from about 30 w/w % to about 80 w/w %, from about 40 w/w % to about 70 w/w %, or from about 50 w/w % to about 60 w/w % of totarol.

A purity of the thujopsene is determined by HPLC. In some cases, HPLC purification is performed as a normal-phase chromatography. In some cases, HPLC purification is performed as a reverse-phase chromatography. In some embodiments, the thujopsene has a purity of about 80%, about 82%, about 84%, about 86%, about 88%, about 90%, about 92%, about 94%, about 95%, or about 100%. In some embodiments, the thujopsene has a purity of at least about 80%, about 82%, about 84%, about 86%, about 88%, about 90%, about 92%, about 94%, about 95%, or about 100%. In some embodiments, the thujopsene has a purity of at most about 80%, about 82%, about 84%, about 86%, about 88%, about 90%, about 92%, about 94%, about 95%, or about 100%. In some embodiments, the thujopsene has a purity of from about 80% to about 100%, from about 82% to about 95%, from about 84% to about 94%, from about 86% to about 92%, or from about 88% to about 90%. In some embodiments, the totarol has a purity of about 80%, about 82%, about 84%, about 86%, about 88%, about 90%, about 92%, about 94%, about 95%, or about 100%. In some embodiments, the totarol has a purity of at least about 80%, about 82%, about 84%, about 86%, about 88%, about 90%, about 92%, about 94%, about 95%, or about 100%. In some embodiments, the totarol has a purity of at most about 80%, about 82%, about 84%, about 86%, about 88%, about 90%, about 92%, about 94%, about 95%, or about 100%. In some embodiments, the totarol has a purity of from about 80% to about 100%, from about 82% to about 95%, from about 84% to about 94%, from about 86% to about 92%, or from about 88% to about 90%.

In some embodiments, the composition further comprises at least one pharmaceutically acceptable carrier, at least one diluent, at least one excipient or at least one additive. In some embodiments, the at least one pharmaceutically acceptable carrier is selected from the group consisting of: dimethyl sulfoxide (DMSO), alpha-thujene, alpha-pinene, camphene, sabinene, beta-pinene, alpha-terpinene, benzene, limonene, peltay2-carene, trans sabinene hydrate, terpinolene, 3-cyclohexen-1-ol, terpinene-4-ol, 1,2-benzenediol, linalyl acetae, borneol, bornyl acetate, alph-thujone, terpinyl acetate, isolongifolene, epit-bicyclosesquiphellandrene, alpha-humulene, guaiol, elemol, cedrol, beta-eudesmol, rosifoliol, rimuene, hexadecanoic acid, cembrene, verticellol, totarol, totara-1,9-octadecenamide, tatarol, 2-(hexyl-thiol)decanal, and combinations thereof. In some embodiments, the at least one diluent comprises buffer, saline, water, DMSO, or combinations thereof. In some embodiments, the at least one excipient is selected from the group consisting of: animal and vegetable fats, oils, waxes, paraffins, starch, tragacanth, cellulose derivatives, polyethylene glycols, silicones, bentonites, silicic acid, talc, zinc oxide, lactose, talc, silicic acid, aluminum hydroxide, calcium silicates, polyamide powder, and combinations thereof. In some embodiments, the at least one additive is selected from the group consisting of: a fatty substance, an organic solvent, a solubilizing agent, a thickener, a gelling agent, a softener, an antioxidant, a suspending agent, a stabilizer, a foaming agent, an aromatic, a surfactant, water, an ionic or non-ionic emulsifying agent, a filler, a sequestering agent, a chelating agent, a preservative, vitamins, a blocker, a moisturizing agent, essential oil, a dye, a pigment, a hydrophilic or hydrophobic activator, a lipid vesicle, antiseptics, stabilizing agents, hydrating agents, emulsification promoters or salts and/or buffers for osmotic control, and combinations thereof.

In some embodiments, the microbial infection comprises a bacterial infection. In some embodiments, the bacterial infection is caused by *Staphylococcus aureus*. In some embodiments, the bacterial infection is caused by methicillin-resistant staph (MRSA), methicillin-susceptible staph (MSSA), or a combination thereof. In some embodiments, the bacterial infection is caused by *Streptococcus*. In some embodiments, the bacterial infection is caused by *Streptococcus pyogenes, Streptococcus dysgalactiae, Streptococcus anginosus*, or a combination thereof. In some embodiments, the composition decreases or reduces the activity of bacteria in the subject.

In some embodiments, administering the composition decreases or reduces the activity of bacteria in the subject. In some embodiments, the activity of bacteria in the subject is decreased or reduced by at least about 10%, 20%, 30%, 40%, 50%, 60%, 70%, 80%, or 90% within 2 hours after the administration. In some embodiments, the activity of bacteria in the subject is decreased or reduced by at most about 10%, 20%, 30%, 40%, 50%, 60%, 70%, 80%, or 90% within 2 hours after the administration. In some embodiments, the activity of bacteria in the subject is decreased or reduced by about 10% to about 90%, about 20% to about 80%, about 30% to about 70%, about 40% to about 60%, or about 50% to 90% within 2 hours after the administration. In some embodiments, the activity of bacteria in the subject is decreased or reduced by at least about 10%, 20%, 30%, 40%, 50%, 60%, 70%, 80%, or 90% within 4 hours after the administration. In some embodiments, the activity of bacteria in the subject is decreased or reduced by at most about 10%, 20%, 30%, 40%, 50%, 60%, 70%, 80%, or 90% within 4 hours after the administration. In some embodiments, the activity of bacteria in the subject is decreased or reduced by about 10% to about 90%, about 20% to about 80%, about 30% to about 70%, about 40% to about 60%, or about 50% to 90% within 4 hours after the administration.

In some embodiments, the composition prevents, inhibits, or slows the destruction of a cell in the subject. In some embodiments, the cell comprises fibroblast. In some embodiments, the therapeutically effective amount of the composition is administered one to five times a day. In some embodiments, the therapeutically effective amount of the composition is administered one, twice, three times, four times or five times a day. In some embodiments, the therapeutically effective amount of the composition is administered one to five times, twice to four times, or three times to five times a day. In some embodiments, the therapeutically effective amount of the composition is administered for at least five consecutive days. In some embodiments, the therapeutically effective amount of the composition is administered for at least six consecutive days. In some embodiments, the therapeutically effective amount of the composition is administered for at least seven consecutive days. In some embodiments, the therapeutically effective amount of the composition is administered for at least five, at least six, or at least seven consecutive days. In some embodiments, the therapeutically effective amount of the composition is administered for at most five, at least six, or at least seven consecutive days. In some embodiments, the therapeutically effective amount of the composition is administered for from five to seven consecutive days. In some embodiments, the therapeutically effective amount of the composition is administered about 15 days, about 21 days, about 24 days, about 28 days, or about 30 days. In some embodiments, the therapeutically effective amount of the composition is administered at most for about 15 days, about 21 days, about 24 days, about 28 days, or about 30 days. In some embodiments, the therapeutically effective amount of the composition is administered for from about 15 days to about 30 days, from about 21 days to about 28 days, or from about 24 days to about 30 days. In some embodiments, the therapeutically effective amount of the composition is administered for from at least about 1 week, at least about 2 weeks, at least about 4 weeks, at least about 2 months, at least about 4 months, or at least about 6 months.

In some embodiments, the therapeutically effective amount of the composition ranges from about 0.001% to about 0.04% of concentration. In some embodiments, the therapeutically effective amount of the composition comprises from about 0.005% to about 0.02% of concentration. In some embodiments, the therapeutically effective amount of the composition comprises from about 0.005% to about 0.04% of concentration. In some embodiments, the therapeutically effective amount of the composition comprises from about 0.01% to about 0.02% of concentration. In some embodiments, the therapeutically effective amount of the composition comprises about 0.001%, about 0.005%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 20%, about 25%, about 30%, about 35%, about 40%, about 45%, or about 50% of concentration. In some embodiments, the therapeutically effective amount of the composition comprises at least about 0.001%, about 0.005%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 20%, about 25%, about 30%, about 35%, about 40%, about 45%, or about 50% of concentration. In some embodiments, the therapeutically effective amount of the composition comprises at most about 0.001%, about 0.005%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 20%, about 25%, about 30%, about 35%, about 40%, about 45%, or about 50% of concentration. In some embodiments, the therapeutically effective amount of the composition comprises from about 0.001% to about 50%, from about 0.005% to about 45%, from about 0.01% to about 40%, from about 0.015% to about 35%, from about 0.02% to about 30%, from about 0.03% to about 25%, from about 0.04% to about 20%, from about 0.05% to about 15%, from about 0.06% to about 14%, from about 0.07% to about 13%, from about 0.08% to about 12%, from about 0.09% to about 11%, from about 0.1% to about 10%, from about 0.2% to about 9%, from about 0.3% to about 8%, from about 0.4% to about 7%, from about 0.5% to about 6%, from about 0.6% to about 5%, from about 0.7% to about 4%, from about 0.8% to about 3%, from about 0.9% to about 2%, or from about 1% to about 50% of concentration. In some embodiments, the therapeutically effective amount of the composition comprises about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 5.0 mg/day, or 10 mg/day. In some embodiments, the therapeutically effective amount of the composition comprises at least about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 5.0 mg/day, or 10 mg/day. In some embodiments, the therapeutically effective amount of the composition comprises at most about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1.0 mg/day, 5.0 mg/day, or 10 mg/day. In some embodiments, the therapeutically effective amount of the composition ranges from about 0.1 mg/day to about 10 mg/day, from about 0.2 mg/day to about 5.0 mg/day, from about 0.3 mg/day to about 1.0 mg/day, from about 0.4 mg/day to about 0.9 mg/day, from about 0.5 mg/day to about 0.8 mg/day, or from about 0.6 mg/day to about 0.7 mg/day.

The therapeutically effective amount of the composition disclosed herein can be administered via topical, transdermal, oral, or nasal administration routes. In some embodiments, the topical administration comprises administration of the composition to an affected skin area. Non-limiting examples of dosage forms for topical administration or for transdermal administration of the composition disclosed herein comprise an ointment, cream, suspensions, paste, lotions, powders, solutions, oils, encapsulated gel, liposomes, sprayable aerosol or vapors, solutions, patches, drops, inhalants, or combinations thereof. In some embodiments, sprayable aerosol or vapors additionally comprise customary propellants, for example chlorofluoro-hydrocarbons, and volatile unsubstituted hydrocarbons, for example butane and propane. In another embodiments, transdermal patches may provide an advantage of controlled delivery of the composition disclosed herein to the subject in need thereof. In some embodiments, the dosage forms are made by dissolving, dispersing or otherwise incorporating the composition disclosed herein in a proper medium. In some embodiments, absorption enhancers are also used to increase the flux of the composition across the skin. In some embodiments, the rate of the flux is controlled by either providing a rate-controlling membrane or dispersing the compound in a polymer matrix or gel. In some embodiments, a drug-impregnated solid carrier (e.g., a dressing) can also be used for topical administration and can be non-naturally occurring.

Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

The terms "subject," "individual," or "patient" are often used interchangeably herein. A "subject" can be a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some cases, the subject is not necessarily diagnosed or suspected of being at high risk for the disease.

The term "in vivo" is used to describe an event that takes place in a subject's body.

The term "ex vivo" is used to describe an event that takes place outside of a subject's body. An ex vivo assay is not performed on a subject. Rather, it is performed upon a sample separate from a subject. An example of an ex vivo assay performed on a sample is an "in vitro" assay.

The term "in vitro" is used to describe an event that takes places contained in a container for holding laboratory reagent such that it is separated from the biological source from which the material is obtained. In vitro assays can encompass cell-based assays in which living or dead cells are employed. In vitro assays can also encompass a cell-free assay in which no intact cells are employed.

As used herein, the term "about" a number refers to that number plus or minus 10% of that number. The term "about" a range refers to that range minus 10% of its lowest value and plus 10% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

"Pharmaceutically acceptable carrier, diluent or excipient" includes without limitation any adjuvant, carrier, excipient, glidant, sweetening agent, diluent, preservative, dye, colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The section headings used herein are for organizational purposes only and are not to be construed as limiting the subject matter described.

The section headings used herein are for organizational purposes only and are not to be construed as limiting the subject matter described.

EXAMPLES

The following examples are included for illustrative purposes only and are not intended to limit the scope of the invention.

Example 1: Thujopsene Kills HSV-1

BS-C-1 African green monkey kidney cells were seeded at $2\times10^5$ cells/well in 24 well plates (Becton Dickinson, Torreyana, CA) and allowed to grow to confluence overnight at 37° C., 5% $CO_2$ in Earle's MEM with 10% fetal calf serum (FCS). To examine the effects of thujopsene, 0, 0.01, and 0.02% of thujopsene were incubated with $2\times10^3$ pfu HSV-1 for 2 or 4 hours, at 37° C. and 5% $CO_2$. For the plaque assay, the medium was removed and wells were overlaid with 0.5 ml 4% buffered formalin, allowed to fix for 10 minutes at room temperature. The formalin was removed and 0.5 ml 0.1% crystal violet in PBS was added to the wells for 5 minutes at room temperature. Wells were then aspirated and the air-dried for visualization of plaques.

Figure 1B:
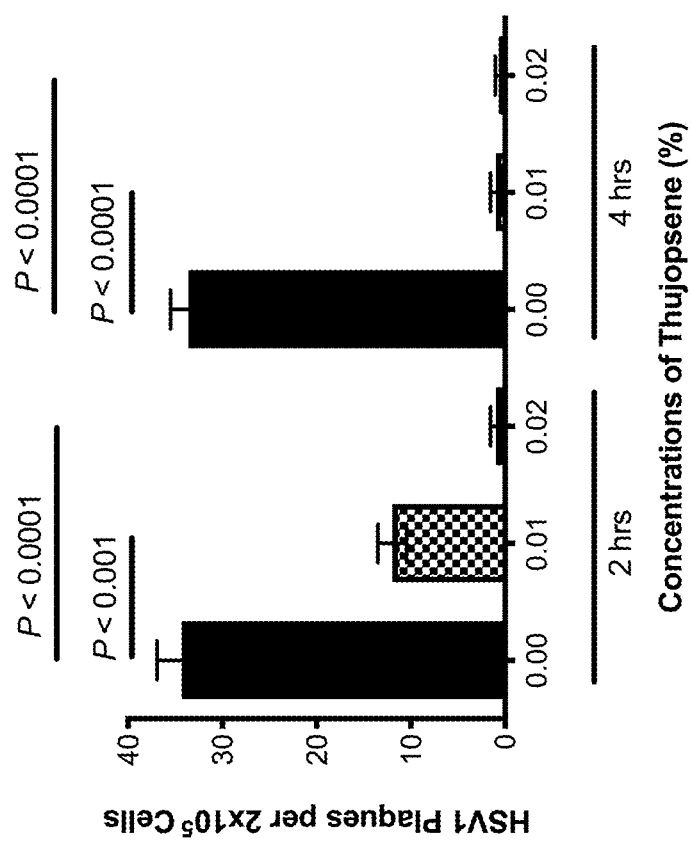

Titers of virus was decreased by at least about 50% after 2-hour incubation with 0.01% thujopsene and was decreased by at least about 90% after either 2-hour incubation with 0.01% thujopsene or 4-hour incubation with 0.01% thujopsene (FIG. 1B).

Example 2: Thujopsene Kills Vaccinia Virus

Vaccinia virus (VV) plaque assay was performed as described above. BS-C-1 African green monkey kidney cells were seeded at $2\times10^5$ cells/well in 24 well plates (Becton Dickinson, Torreyana, CA) and allowed to grow to confluence overnight at 37° C., 5% $CO_2$ in Earle's MEM with 10% fetal calf serum (FCS). To examine the effects of thujopsene, 0, 0.01, and 0.02% of thujopsene were incubated with $2\times10^3$ pfu VV for 2 or 4 hours, at 37° C. and 5% $CO_2$. For the plaque assay, the medium was removed and wells were overlaid with 0.5 ml 4% buffered formalin, allowed to fix for 10 minutes at room temperature. The formalin was removed and 0.5 ml 0.1% crystal violet in PBS was added to the wells for 5 minutes at room temperature. Wells were then aspirated and the air-dried for visualization of plaques.

Figure 2A:
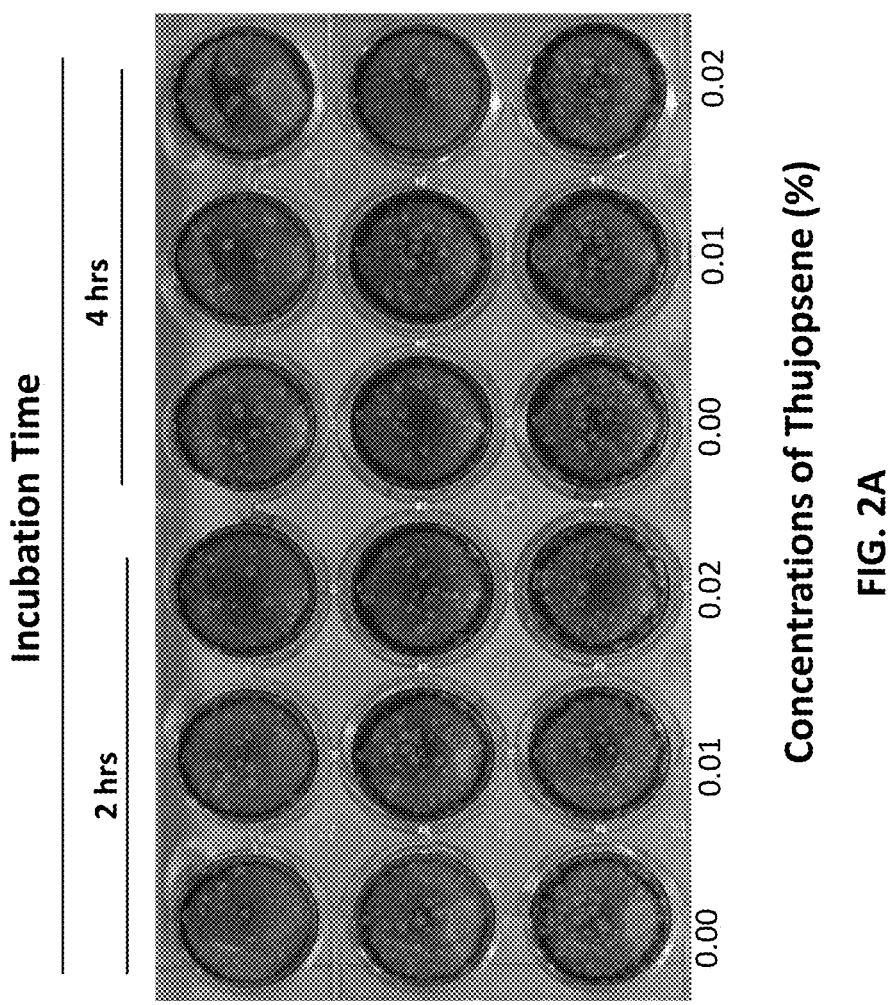
FIGS. 2A and 2B show results of plaque assay after incubations of vaccinia virus with various concentrations of thujopsene for 2 or 4 hours.
Figure 2B:
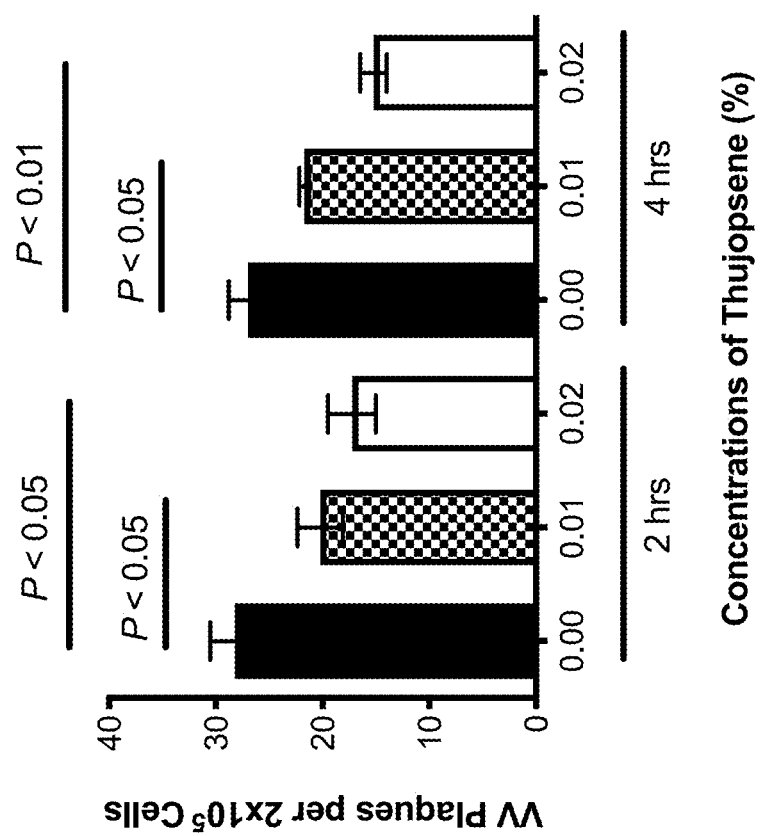

Titers of virus was decreased by at least about 25% after either 2-hour incubation with 0.02% thujopsene or 4-hour incubation with 0.02% thujopsene (FIG. 2B).

Figure 3:
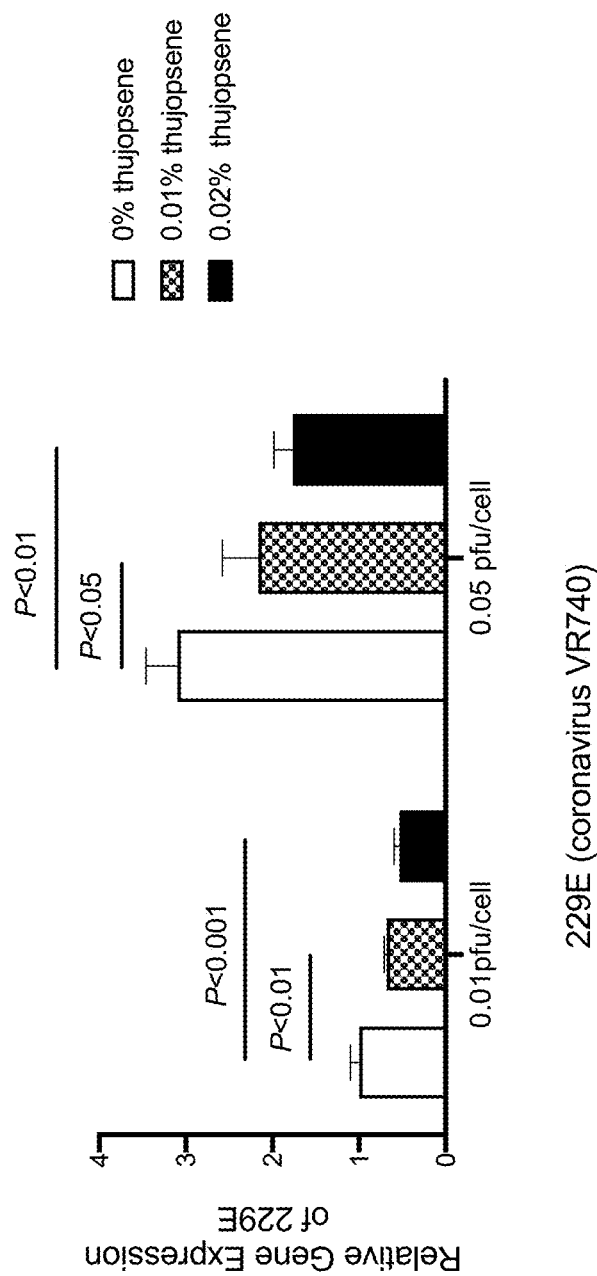
FIG. 3 shows relative gene expression of coronavirus (229E-VR740) with various concentrations of thujopsene.

Example 3: Thujopsene Inhibits Replication of Coronavirus (229E-VR740) in Human Fibroblasts Human fibroblasts (Atcc.org, CCL-191) were treated with coronavirus (229E) and 0.01% or 0.02% of thujopsene for 24 hours, and then RNAs were isolated and PCRs were performed. Total RNA was isolated according to manufacturer's guidelines. RNeasy Mini Kits (Qiagen, Germantown, MD) were used according to the manufacturer's protocol to isolate RNA. RNA was reverse transcribed into cDNA using SuperScript® VILO™ MasterMix according to manufacturer's protocol and DNA was isolated according to manufacturer's guidelines. cDNAs were analyzed by real time RT-PCR by using an ABI Prism 7300 sequence detector. FIG. 3 demonstrates relative gene expression of 229E (coronavirus VR740) decreased in a dose-dependent manner for both cases of 0.01 pfu/cell and 0.05 pfu/cell.

Figure 4:
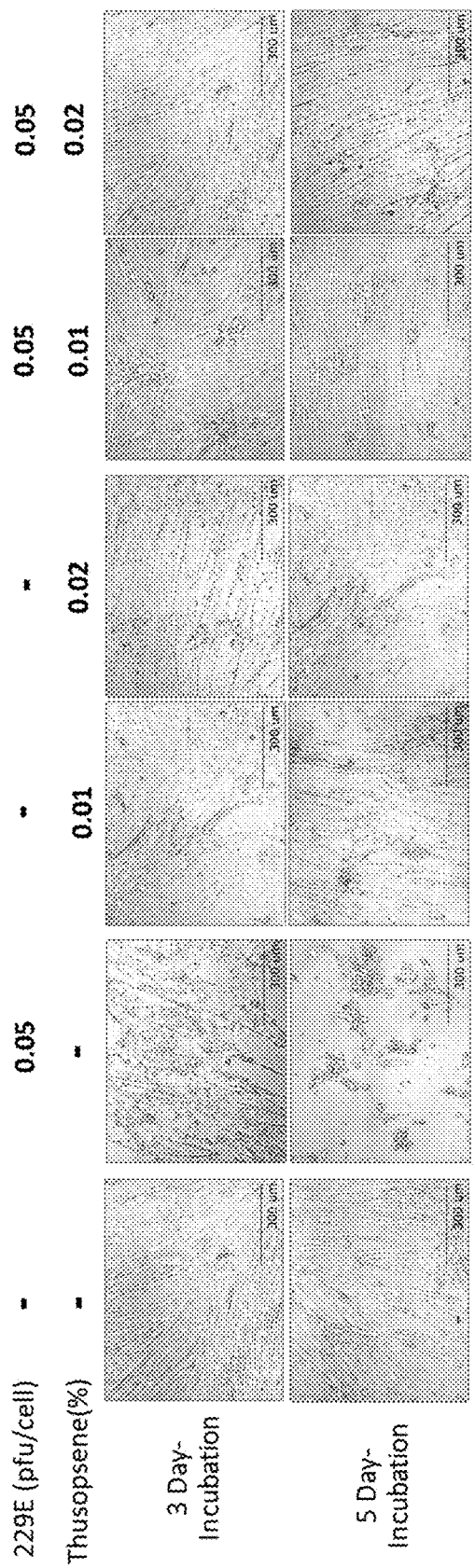
FIG. 4 shows coronavirus 229E (VR-740)-mediated destruction of human fibroblast with various concentrations of thujopsene.

Example 4: Thujopsene Prevents Coronavirus 229E (VR-740)-Mediated Destruction of Human Fibroblast Normal human lung fibroblst (ATCC.org, CCL-191) were seeded at $1 \times 10^5$ cells/well in 24 well plates (Becton Dickinson, Torreyana, CA) and allowed to grow to confluence overnight at 37° C., 5% $CO_2$ in Earle's MEM with 10% fetal calf serum (FCS). To examine whether thujopsene prevents coronavirus (229E)-induced destruction of fibroblast, fibroblasts were incubated with thujopsene (0.00, 0.01 or 0.02%) and 229E (0.05 pfu/cell) for 3 days or 5 days at 37° C. and 5% $CO_2$. Then cell images (×25 magnification) were taken with the microscopy (Leica, Wetzler, Germany). With an incubation of 0.01% or 0.02% thujopsene, the cellular structures were maintained after the treatment with coronavirus 229E. FIG. 4 demonstrates that thujopsene prevented coronavirus mediated destruction of the cellular structure.

Example 5: Thujopsene has Synergistic Effects with Totarol to Kill Bacteria

Experiments were conducted using bacteria including methicillin-sensitive *S. aureus* (MSSA) (ATCC BAA-29213, Manassas, VA), methicillin-resistant *S. aureus* (MRSA) (ATCC BAA-1556), and *Streptococcus pyogenes* (ATCC BAA-19615). Bacterial cultures were grown overnight in Tryptic Soy Broth (Becton Dickinson, Franklin Lakes, NJ) at 37° C. and reseeded in fresh medium three hours prior to experiment. Bacterial concentration was determined by optical density. Bacteria were incubated with vehicle, thujopsene (0.001%), totarol (0.0001%), or a combination of thujopsene (0.001%) and totarol (0.0001%) for 2 hours at 37° C. while shaking, then plated on Tryptic Soy Agar plates and incubated overnight at 37° C. Multiple dilutions were made for each sample to ensure that there were a measurable number of colonies on a given plate. Colonies were counted the following day.

Figure 5:
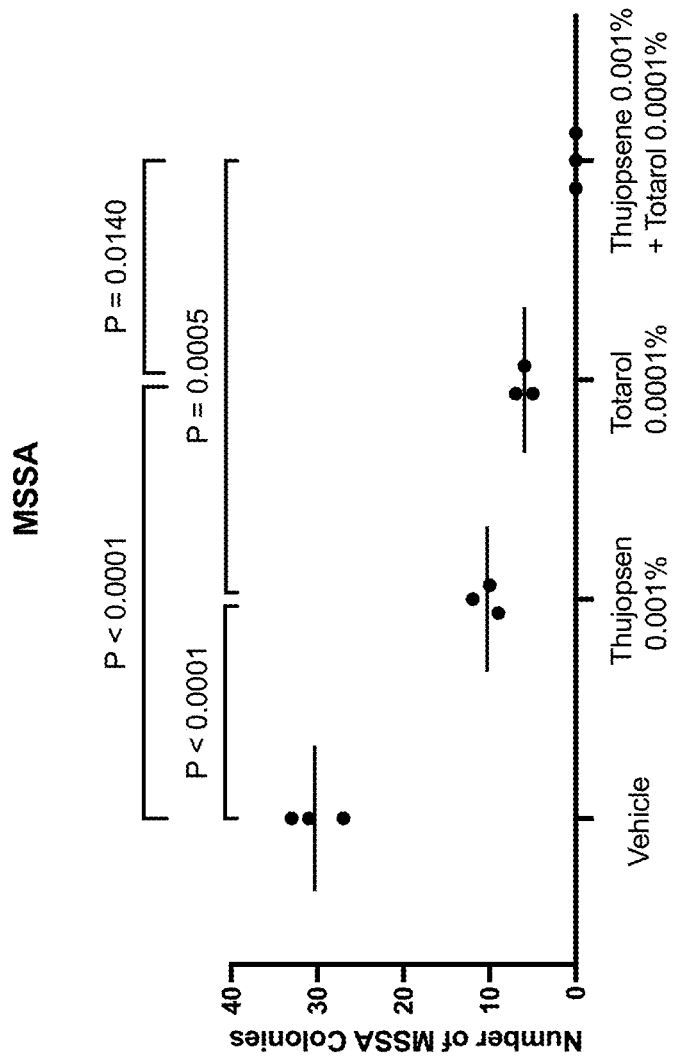
FIG. 5 shows results of viral titer assay after incubations of MSSA with vehicle (DMSO), thujopsene, totarol, or a combination thereof.
Figure 6:
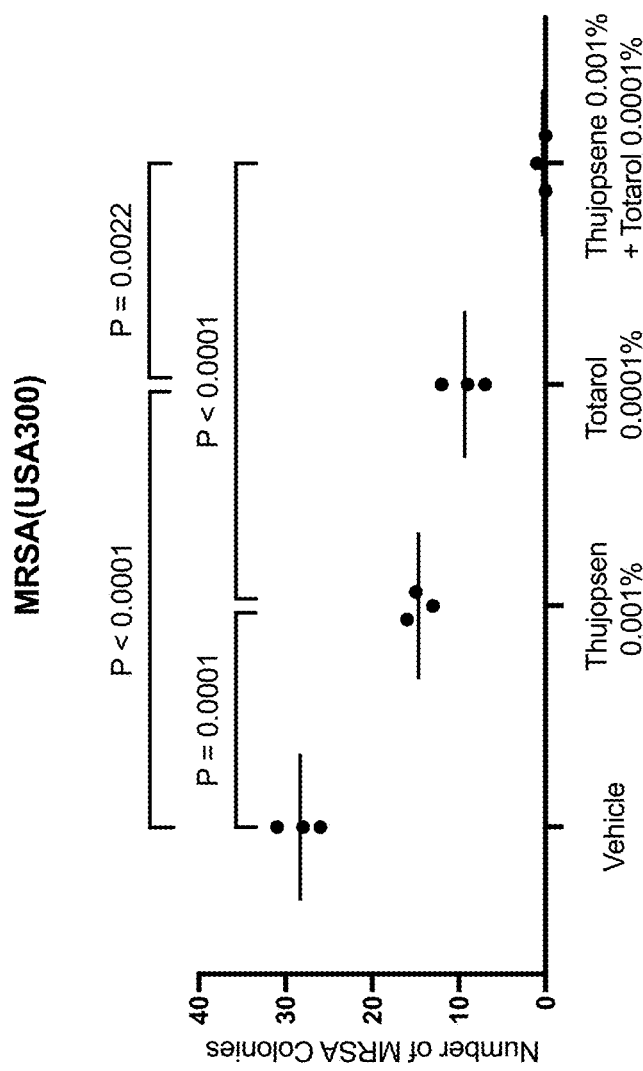
FIG. 6 shows results of viral titer assay after incubations of MRSA (USA300) with vehicle (DMSO), thujopsene, totarol, or a combination thereof.
Figure 7:
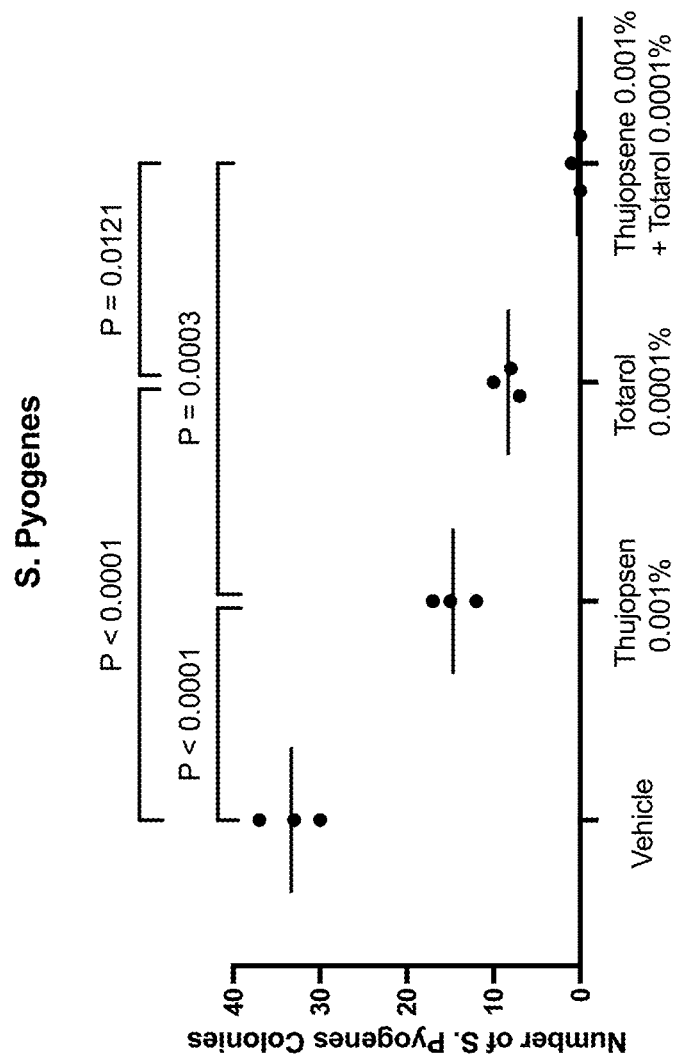
FIG. 7 shows results of viral titer assay after incubations of S. pyogenes with vehicle (DMSO), thujopsene, totarol, or a combination thereof.

This example demonstrates that the purified thujopsene, the purified totarol, or the mixture thereof inhibits bacterial activity. Inhibitory effects of the mixture on bacteria were analyzed using the bactericidal assay. MSSA was significantly ($P<0.0001$) inhibited by the purified thujopsene, the purified totarol, or the mixture thereof with concentration as low as 0.0001% (FIG. 5). MRSA was also significantly ($P<0.0001$) inhibited by the purified thujopsene, the purified totarol, or the mixture thereof with concentration as low as 0.0001% (FIG. 6). *S. pyogenes* was significantly inhibited by thujopsene, totarol, or the mixture thereof with concentration as low as 0.0001% (FIG. 7) as well.

LIST OF EMBODIMENTS

The following list of embodiments of the invention are to be considered as disclosing various features of the invention, which features can be considered to be specific to the particular embodiment under which they are discussed, or which are combinable with the various other features as listed in other embodiments. Thus, simply because a feature is discussed under one particular embodiment does not necessarily limit the use of that feature to that embodiment.

Embodiment 1. A method for treating a viral infection in a subject in need thereof, the method comprising administering to the subject a therapeutically effective amount of a composition comprising at least about 10% of thujopsene.

Embodiment 2. The method of embodiment 1, wherein the composition comprises at least about 30% of thujopsene.

Embodiment 3. The method of embodiment 1, wherein the composition comprises at least about 50% of thujopsene.

Embodiment 4. The method of embodiment 1, wherein the composition comprises at least about 70% of thujopsene.

Embodiment 5. The method of embodiment 1, wherein the composition comprises at least about 90% of thujopsene.

Embodiment 6. The method of embodiment 1, wherein the thujopsene has a purity of at least about 80%.

Embodiment 7. The method of embodiment 1, wherein the thujopsene has a purity of at least about 90%.

Embodiment 8. The method of embodiment 1, wherein the thujopsene has a purity of at least about 95%.

Embodiment 9. The method of embodiment 1, wherein the purity of thujopsene is determined by HPLC.

Embodiment 10. The method of embodiment 1, wherein the viral infection is caused by a herpesvirus (HSV).

Embodiment 11. The method of embodiment 10, wherein the HSV comprises HSV-1, HSV-2, varicella-zoster virus (VZV), Epstein-Barr virus (EBV), human cytomegalovirus (HCMV), human herpesvirus 6A (HHV-6A), human herpesvirus 6B (HHV-6B), human herpesvirus 7 (HHV-7), or Kaposi's sarcoma-associated herpesvirus (KSHV).

Embodiment 12. The method of embodiment 1, wherein the viral infection is caused by a poxvirus.

Embodiment 13. The method of embodiment 12, wherein the poxvirus comprises smallpox virus (variola), vaccinia virus, cowpox virus, monkeypox virus, orf virus, pseudo-cowpox virus, bovine popular stomatitis virus, tanapox virus, yaba monkey tumor virus, or molluscum contagiosum virus.

Embodiment 14. The method of embodiment 1, wherein the viral infection is caused by a coronavirus.

Embodiment 15. The method of embodiment 14, wherein the coronavirus comprises 229E, NL63, OC43, or HKU1.

Embodiment 16. The method of embodiment 14, wherein the coronavirus comprises MFRS-CoV, SARS-CoV, SARS-CoV-2, or a variant thereof.

Embodiment 17. The method of embodiment 1, wherein administering the composition decreases or reduces viral titer in the subject.

Embodiment 18. The method of embodiment 17, wherein the viral titer in the subject is measured by determining the number of plaque forming units (pfu) in a cell in the subject.

Embodiment 19. The method of embodiment 17, wherein the viral titer in the subject is decreased or reduced by at least about 10%, 20%, 30%, 40%, 50%, 60%, 70%, 80%, or 90% within 2 hours after the administration.

Embodiment 20. The method of embodiment 17, wherein the viral titer in the subject is decreased or reduced by at least about 10%, 20%, 30%, 40%, 50%, 60%, 70%, 80%, or 90% within 4 hours after the administration.

Embodiment 21. The method of embodiment 1, wherein the composition decreases or reduces the activity of viruses in the subject.

Embodiment 22. The method of embodiment 21, wherein the activity of viruses in the subject is decreased or reduced by at least about 10%, 20%, 30%, 40%, 50%, 60%, 70%, 80%, or 90% within 2 hours after the administration.

Embodiment 23. The method of embodiment 21, wherein the activity of viruses in the subject is decreased or reduced by at least about 10%, 20%, 30%, 40%, 50%, 60%, 70%, 80%, or 90% within 4 hours after the administration.

Embodiment 24. The method of embodiment 1, wherein the composition decreases or reduces viral gene expression in the subject.

Embodiment 25. The method of embodiment 24, wherein the gene expression of viruses in the subject is decreased or reduced by at least about 10%, 20%, 30%, 40%, 50%, 60%, 70%, 80%, or 90% within 2 hours after the administration.

Embodiment 26. The method of embodiment 24, wherein the gene expression of viruses in the subject is decreased or reduced by at least about 10%, 20%, 30%, 40%, 50%, 60%, 70%, 80%, or 90% within 4 hours after the administration.

Embodiment 27. The method of embodiment 1, wherein the composition prevents, inhibits, or slows the destruction of a cell in the subject.

Embodiment 28. The method of embodiment 27, wherein the cell comprises fibroblast.

Embodiment 29. The method of embodiment 1, wherein the therapeutically effective amount of the composition is administered one to five times a day.

Embodiment 30. The method of embodiment 1, wherein the therapeutically effective amount of the composition is administered two times a day.

Embodiment 31. The method of embodiment 1, wherein the therapeutically effective amount of the composition is administered three times a day.

Embodiment 32. The method of embodiment 1, wherein the therapeutically effective amount of the composition is administered for at least five consecutive days.

Embodiment 33. The method of embodiment 1, wherein the therapeutically effective amount of the composition is administered for at least seven consecutive days.

Embodiment 34. The method of embodiment 1, wherein the therapeutically effective amount of the composition is administered at least for about 15 days, about 21 days, about 24 days, about 28 days, or about 30 days.

Embodiment 35. The method of embodiment 1, wherein the therapeutically effective amount of the composition comprises from about 0.001% to about 0.04% of concentration.

Embodiment 36. The method of embodiment 1, wherein the therapeutically effective amount of the composition comprises from about 0.005% to about 0.02% of concentration.

Embodiment 37. The method of embodiment 1, wherein the therapeutically effective amount of the composition comprises from about 0.005% to about 0.04% of concentration.

Embodiment 38. The method of embodiment 1, wherein the therapeutically effective amount of the composition comprises from about 0.01% to about 0.02% of concentration.

Embodiment 39. The method of embodiment 1, wherein the administering comprises topical administration or transdermal administration.

Embodiment 40. The method of embodiment 39, wherein the topical administration comprises administration of the composition to an affected skin area.

Embodiment 41. The method of embodiment 39, wherein the topical administration comprises administering an ointment, cream, suspensions, paste, lotions, powders, solutions, oils, encapsulated gel, liposomes, sprayable aerosol or vapors, or any combination thereof.

Embodiment 42. A pharmaceutical composition for treating a microbial infection in a subject in need thereof, the composition comprising thujopsene and totarol, wherein the composition comprises at least about 10% of thujopsene and at least about 10% of totarol.

Embodiment 43. The pharmaceutical composition of embodiment 42, wherein the total volume amount of thujopsene and totarol in the composition comprises at least about 20%, 40%, 60%, 80%, or 90%.

Embodiment 44. The pharmaceutical composition of embodiment 42, wherein the volume amount of thujopsene is higher than the volume amount of totarol.

Embodiment 45. The pharmaceutical composition of embodiment 42, wherein the thujopsene has a purity of at least about 80%.

Embodiment 46. The pharmaceutical composition of embodiment 42, wherein the thujopsene has a purity of at least about 90%.

Embodiment 47. The pharmaceutical composition of embodiment 42, wherein the thujopsene has a purity of at least about 95%.

Embodiment 48. The pharmaceutical composition of embodiment 42, wherein the totarol has a purity of at least about 80%.

Embodiment 49. The pharmaceutical composition of embodiment 42, wherein the totarol has a purity of at least about 90%.

Embodiment 50. The pharmaceutical composition of embodiment 42, wherein the totarol has a purity of at least about 95%.

Embodiment 51. The pharmaceutical composition of embodiment 42, wherein the purity of thujopsene is determined by HPLC.

Embodiment 52. The pharmaceutical composition of embodiment 42, wherein the composition further comprises at least one pharmaceutically acceptable carrier, at least one diluent, at least one excipient or at least one additive.

Embodiment 53. The pharmaceutical composition of embodiment 52, wherein the at least one pharmaceutically acceptable carrier is selected from the group consisting of: dimethyl sulfoxide (DMSO), alpha-thujene, alpha-pinene, camphene, sabinene, beta-pinene, alpha-terpinene, benzene, limonene, peltay2-carene, trans sabinene hydrate, terpinolene, 3-cyclohexen-1-01, terpinene-4-ol, 1,2-benzenediol, linalyl acetae, borneol, bornyl acetate, alph-thujone, terpinyl acetate, isolongifolene, epit-bicyclosesquiphellandrene, alpha-humulene, guaiol, elemol, cedrol, beta-eudesmol, rosifoliol, rimuene, hexadecanoic acid, cembrene, verticellol, totarol, totara-1,9-octadecenamide, tatarol, 2-(hexylthiol)decanal, and combinations thereof.

Embodiment 54. The pharmaceutical composition of embodiment 52, wherein the at least one diluent comprises buffer, saline, water, DMSO, lactose, or combinations thereof.

Embodiment 55. The pharmaceutical composition of embodiment 52, wherein the at least one excipient is selected from the group consisting of: animal and vegetable fats, oils, waxes, paraffins, starch, tragacanth, cellulose derivatives, polyethylene glycols, silicones, bentonites, silicic acid, talc, zinc oxide, lactose, talc, silicic acid, aluminum hydroxide, calcium silicates, polyamide powder, and combinations thereof.

Embodiment 56. The pharmaceutical composition of embodiment 52, wherein the at least one additive is selected from the group consisting of: a fatty substance, an organic solvent, a solubilizing agent, a thickener, a gelling agent, a softener, an antioxidant, a suspending agent, a stabilizer, a foaming agent, an aromatic, a surfactant, water, an ionic or non-ionic emulsifying agent, a filler, a sequestering agent, a chelating agent, a preservative, vitamins, a blocker, a moisturizing agent, essential oil, a dye, a pigment, a hydrophilic or hydrophobic activator, a lipid vesicle, antiseptics, stabilizing agents, hydrating agents, emulsification promoters or salts and/or buffers for osmotic control, and combinations thereof.

Embodiment 57. The pharmaceutical composition of embodiment 42, wherein the microbial infection comprises a bacterial infection.

Embodiment 58. The pharmaceutical composition of embodiment 57, wherein the bacterial infection is caused by *Staphylococcus aureus*.

Embodiment 59. The pharmaceutical composition of embodiment 57, wherein the bacterial infection is caused by methicillin-resistant staph (MRSA), methicillin-susceptible staph (MSSA), or a combination thereof.

Embodiment 60. The pharmaceutical composition of embodiment 57, wherein the bacterial infection is caused by *Streptococcus*.

Embodiment 61. The pharmaceutical composition of embodiment 57, wherein the bacterial infection is caused by *Streptococcus pyogenes, Streptococcus dysgalactiae, Streptococcus anginosus*, or a combination thereof.

Embodiment 62. A method for treating a microbial infection in a subject in need thereof, the method comprising administering to the subject a therapeutically effective amount of a composition comprising thujopsene and totarol, wherein the composition comprises at least about 10% of thujopsene and at least about 10% of totarol.

Embodiment 63. The method of embodiment 62, wherein the total volume amount of thujopsene and totarol in the composition comprises at least about 20%, 40%, 60%, 80%, or 90%.

Embodiment 64. The method of embodiment 63, wherein the volume amount of thujopsene is higher than the volume amount of totarol.

Embodiment 65. The method of embodiment 63, wherein the thujopsene has a purity of at least about 80%.

Embodiment 66. The method of embodiment 63, wherein the thujopsene has a purity of at least about 90%.

Embodiment 67. The method of embodiment 63, wherein the thujopsene has a purity of at least about 95%.

Embodiment 68. The method of embodiment 63, wherein the totarol has a purity of at least about 80%.

Embodiment 69. The method of embodiment 63, wherein the totarol has a purity of at least about 90%.

Embodiment 70. The method of embodiment 63, wherein the totarol has a purity of at least about 95%.

Embodiment 71. The method of embodiment 63, wherein the purity of thujopsene is determined by HPLC.

Embodiment 72. The method of embodiment 63, wherein the composition further comprises at least one pharmaceutically acceptable carrier, at least one diluent, at least one excipient or at least one additive.

Embodiment 73. The method of embodiment 72, wherein the at least one pharmaceutically acceptable carrier is selected from the group consisting of: dimethyl sulfoxide (DMSO), alpha-thujene, alpha-pinene, camphene, sabinene, beta-pinene, alpha-terpinene, benzene, limonene, peltay2-carene, trans sabinene hydrate, terpinolene, 3-cyclohexen-1-ol, terpinene-4-ol, 1,2-benzenediol, linalyl acetae, borneol, bornyl acetate, alph-thujone, terpinyl acetate, isolongifolene, epit-bicyclosesquiphellandrene, alpha-humulene, guaiol, elemol, cedrol, beta-eudesmol, rosifoliol, rimuene, hexadecanoic acid, cembrene, verticellol, totarol, totara-1,9-octadecenamide, tatarol, 2-(hexylthiol)decanal, and combinations thereof.

Embodiment 74. The method of embodiment 72, wherein the at least one diluent comprises buffer, saline, water, DMSO, lactose, or combinations thereof.

Embodiment 75. The method of embodiment 72, wherein the at least one excipient is selected from the group consisting of: animal and vegetable fats, oils, waxes, paraffins, starch, tragacanth, cellulose derivatives, polyethylene glycols, silicones, bentonites, silicic acid, talc, zinc oxide, lactose, talc, silicic acid, aluminum hydroxide, calcium silicates, polyamide powder, and combinations thereof.

Embodiment 76. The method of embodiment 72, wherein the at least one additive is selected from the group consisting of: a fatty substance, an organic solvent, a solubilizing agent, a thickener, a gelling agent, a softener, an antioxidant, a suspending agent, a stabilizer, a foaming agent, an aromatic, a surfactant, water, an ionic or non-ionic emulsifying agent, a filler, a sequestering agent, a chelating agent, a preservative, vitamins, a blocker, a moisturizing agent, essential oil, a dye, a pigment, a hydrophilic or hydrophobic activator, a lipid vesicle, antiseptics, stabilizing agents, hydrating agents, emulsification promoters or salts and/or buffers for osmotic control, and combinations thereof.

Embodiment 77. The method of embodiment 62, wherein the microbial infection comprises a bacterial infection.

Embodiment 78. The method of embodiment 77, wherein the bacterial infection is caused by *Staphylococcus aureus*.

Embodiment 79. The method of embodiment 77, wherein the bacterial infection is caused by methicillin-resistant staph (MRSA), methicillin-susceptible staph (MSSA), or a combination thereof.

Embodiment 80. The method of embodiment 77, wherein the bacterial infection is caused by *Streptococcus*.

Embodiment 81. The method of embodiment 77, wherein the bacterial infection is caused by *Streptococcus pyogenes, Streptococcus dysgalactiae, Streptococcus anginosus*, or a combination thereof.

Embodiment 82. The method of embodiment 62, wherein the composition decreases or reduces the activity of bacteria in the subject.

Embodiment 83. The method of embodiment 82, wherein the activity of bacteria in the subject is decreased or reduced by at least about 10%, 20%, 30%, 40%, 50%, 60%, 70%, 80%, or 90% within 2 hours after the administration.

Embodiment 84. The method of embodiment 82, wherein the activity of bacteria in the subject is decreased or reduced by at least about 10%, 20%, 30%, 40%, 50%, 60%, 70%, 80%, or 90% within 4 hours after the administration.

Embodiment 85. The method of embodiment 62, wherein the therapeutically effective amount of the composition is administered one to five times a day.

Embodiment 86. The method of embodiment 62, wherein the therapeutically effective amount of the composition is administered two times a day.

Embodiment 87. The method of embodiment 62, wherein the therapeutically effective amount of the composition is administered three times a day.

Embodiment 88. The method of embodiment 62, wherein the therapeutically effective amount of the composition is administered for at least five consecutive days.

Embodiment 89. The method of embodiment 62, wherein the therapeutically effective amount of the composition is administered for at least seven consecutive days.

Embodiment 90. The method of embodiment 62, wherein the therapeutically effective amount of the composition is administered at least for about 15 days, about 21 days, about 24 days, about 28 days, or about 30 days.

Embodiment 91. The method of embodiment 62, wherein the therapeutically effective amount of the composition comprises from about 0.001% to about 0.04% of concentration.

Embodiment 92. The method of embodiment 62, wherein the therapeutically effective amount of the composition comprises from about 0.005% to about 0.02% of concentration.

Embodiment 93. The method of embodiment 62, wherein the therapeutically effective amount of the composition comprises from about 0.005% to about 0.04% of concentration.

Embodiment 94. The method of embodiment 62, wherein the therapeutically effective amount of the composition comprises from about 0.01% to about 0.02% of concentration.

Embodiment 95. The method of embodiment 62, wherein the administering comprises topical administration or transdermal administration.

Embodiment 96. The method of embodiment 95, wherein the topical administration comprises administration of the composition to an affected skin area.

Embodiment 97. The method of embodiment 96, wherein the topical administration comprises administering an ointment, cream, suspensions, paste, lotions, powders, solutions, oils, encapsulated gel, liposomes, sprayable aerosol or vapors, or any combination thereof.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating a viral infection caused by a poxvirus in a subject in need thereof, the method comprising administering to the subject a therapeutically effective amount of a composition comprising at least about 10% of thujopsene.

2. The method of claim 1, wherein the composition comprises at least about 30, 50, 70, or 90% of thujopsene.

3. The method of claim 1, wherein the thujopsene has a purity of at least about 80, 90, or 95%.

4. The method of claim 1, wherein the poxvirus comprises smallpox virus (variola), vaccinia virus, cowpox virus, monkeypox virus, orf virus, pseudocowpox virus, bovine popular stomatitis virus, tanapox virus, yaba monkey tumor virus, or molluscum contagiosum virus.

5. The method of claim 1, wherein administering the composition decreases or reduces viral titer in the subject, wherein the viral titer in the subject is measured by determining the number of plaque forming units (pfu) in a cell in the subject.

6. The method of claim 5, wherein the viral titer in the subject is decreased or reduced by at least about 10%, 20%, 30%, 40%, 50%, 60%, 70%, 80%, or 90% within 2 or 4 hours after the administration.

7. The method of claim 1, wherein the composition decreases or reduces activity of viruses in the subject, wherein the activity of viruses in the subject is decreased or reduced by at least about 10%, 20%, 30%, 40%, 50%, 60%, 70%, 80%, or 90% within 2 or 4 hours after the administration.

8. The method of claim 1, wherein the composition decreases or reduces gene expression of viruses in the subject, wherein the gene expression of viruses in the subject is decreased or reduced by at least about 10%, 20%, 30%, 40%, 50%, 60%, 70%, 80%, or 90% within 2 or 4 hours after the administration.

9. The method of claim 1, wherein the composition prevents, inhibits, or slows the destruction of a cell in the subject.

10. The method of claim 9, wherein the cell comprises fibroblast.

11. The method of claim 1, wherein the therapeutically effective amount of the composition is administered one to five times a day.

12. The method of claim 1, wherein the therapeutically effective amount of the composition is administered for at least about 5 days, about 7 days, about 15 days, about 21 days, about 24 days, about 28 days, or about 30 days.

13. The method of claim 1, wherein the therapeutically effective amount of the composition is at a concentration of from about 0.0010% to about 0.04%.

14. The method of claim 1, wherein the administering comprises topical administration or transdermal administration.

* * * * *